(12) United States Patent
Chaum et al.

(10) Patent No.: US 9,983,162 B2
(45) Date of Patent: May 29, 2018

(54) METHOD AND DEVICE FOR DETECTION OF BIOAVAILABLE DRUG CONCENTRATION

(71) Applicants: THE UNIVERSITY OF TENNESSEE RESEARCH FOUNDATION, Knoxville, TN (US); THE UNIVERSITY OF MEMPHIS RESEARCH FOUNDATION, Memphis, TN (US)

(72) Inventors: Edward Chaum, Memphis, TN (US); Erno Lindner, Germantown, TN (US); Jidong Guo, Chungdhun (CN)

(73) Assignees: THE UNIVERSITY OF TENNESSEE RESEARCH FOUNDATION, Knoxville, TN (US); THE UNIVERSITY OF MEMPHIS RESEARCH FOUNDATION, Memphis, TN (US)

(*) Notice: Subject to any disclaimer, the term of this patent is extended or adjusted under 35 U.S.C. 154(b) by 259 days.

(21) Appl. No.: 14/404,674

(22) PCT Filed: Mar. 14, 2013

(86) PCT No.: PCT/US2013/031747
§ 371 (c)(1),
(2) Date: Dec. 1, 2014

(87) PCT Pub. No.: WO2013/180814
PCT Pub. Date: Dec. 5, 2013

(65) Prior Publication Data
US 2015/0119848 A1 Apr. 30, 2015

Related U.S. Application Data

(60) Provisional application No. 61/654,469, filed on Jun. 1, 2012.

(51) Int. Cl.
*G01N 27/327* (2006.01)
*A61M 5/142* (2006.01)
(Continued)

(52) U.S. Cl.
CPC .......... *G01N 27/3275* (2013.01); *A61M 5/142* (2013.01); *A61M 5/1723* (2013.01); *G01N 27/333* (2013.01); *A61M 2202/048* (2013.01)

(58) Field of Classification Search
CPC ............. G01N 27/3275; G01N 27/333; G01N 27/3335
See application file for complete search history.

(56) References Cited

U.S. PATENT DOCUMENTS 4,053,381 A 10/1977 Hamblen et al.
4,280,494 A 7/1981 Cosgrove, Jr. et al.
(Continued)

FOREIGN PATENT DOCUMENTS

WO 2006040588 A1 4/2006
WO 2008030582 A2 3/2008
(Continued)

OTHER PUBLICATIONS

Justin M. Zook, Jan Langmaier, Ernő Lindner, Current-polarized ion-selective membranes: The influence of plasticizer and lipophilic background electrolyte on concentration profiles, resistance, and voltage transients, Sensors and Actuators B: Chemical, vol. 136, Issue 2, Mar. 2, 2009, pp. 410-418, ISSN 0925-4005, http://dx.doi.org/10.1016/j.snb.*

(Continued)

*Primary Examiner* — Louis J Rufo
(74) *Attorney, Agent, or Firm* — Baker Donelson

(57) ABSTRACT

The present invention is directed to an electrochemical sensor involving an electrode and a coating that surrounds the electrode, the coating comprising a structural compo-
(Continued)

nent, a water immiscible solvent, a resistance decreasing component, and an ion exchange component, wherein the coating selectively partitions an electrochemically active drug from a fluid or vapor sample whereby an electrochemical signal within the coating can be measured using the electrode. Devices and methods for using this electrochemical sensor are also disclosed.

13 Claims, 15 Drawing Sheets

(51) Int. Cl.
  A61M 5/172      (2006.01)
  G01N 27/333     (2006.01)

(56) References Cited

U.S. PATENT DOCUMENTS

| | | |
|---|---|---|
| 4,533,346 A | 8/1985 | Cosgrove, Jr. et al. |
| 4,869,264 A | 9/1989 | Silberstein |
| 5,094,235 A | 3/1992 | Westenskow et al. |
| 5,212,050 A | 5/1993 | Mier et al. |
| 5,554,339 A | 9/1996 | Cozzette et al. |
| 5,649,531 A | 7/1997 | Heinonen |
| 5,830,341 A | 11/1998 | Gilmartin |
| 6,631,291 B2 | 10/2003 | Viertio-Oja et al. |
| 6,646,071 B1 | 11/2003 | Klosin et al. |
| 6,691,705 B2 | 2/2004 | Dittmann et al. |
| 6,745,764 B2 | 6/2004 | Hickle |
| 6,757,558 B2 | 6/2004 | Lange et al. |
| 7,220,240 B2 | 5/2007 | Struys et al. |
| 7,364,552 B2 | 4/2008 | Kiesele et al. |
| 2003/0209450 A1 | 11/2003 | McVey et al. |
| 2003/0212441 A1 | 11/2003 | Starkweather et al. |
| 2004/0103897 A1 | 6/2004 | Hickle et al. |
| 2004/0217017 A1 | 11/2004 | Kidwell |
| 2006/0167722 A1 | 7/2006 | Struys et al. |
| 2007/0118075 A1 | 5/2007 | Uutela et al. |
| 2007/0134721 A1 | 6/2007 | Laitenberger et al. |
| 2007/0203448 A1 | 8/2007 | Melker et al. |
| 2008/0000290 A1 | 1/2008 | Nagels et al. |
| 2008/0176271 A1 | 7/2008 | Silver |
| 2008/0200789 A1 | 8/2008 | Brister et al. |
| 2009/0177146 A1 | 7/2009 | Nesbitt et al. |
| 2010/0173421 A1 | 7/2010 | Piletsky et al. |
| 2012/0116195 A1 | 5/2012 | Chaum et al. |

FOREIGN PATENT DOCUMENTS

| | | | |
|---|---|---|---|
| WO | 2010045465 A1 | 4/2010 | |
| WO | WO 2010045465 A1 * | 4/2010 | ......... A61B 5/14546 |

OTHER PUBLICATIONS

PCT International Search Report and Written Opinion for PCT/US2013/031747, filed Mar. 14, 2013 (dated Jul. 15, 2013).
Wang et al. "New Target Controlled Infusion Using a Hybrid Physiologically Based Pharmacokinetic Model," The 2nd International Conference on Bioinformatics and Biomedical Engineering, Shanghai, China, May 16-18, 2008, (978-1-4244-1748-3/08) (EI, IEEE Xplore).
Geertsma et al. "New and Emerging Medical Technologies: A Horizon Scan of Opportunities and Risks," RIVM Report 65/07:59-63 (2007).
Toth et al. "Electrochemical Detection in Liquid Flow Analytical Techniques: Characterization and Classification," Pure Appl Chem 76(6):1119-1138 (2004).
Van Poucke et al. "Target Controlled Infusions: Targeting the Effect Site While Limiting Peak Plasma Concentration," IEEE Transactions on Biomedical Engineering 51(11):1869-1875 (2004).
Enlund, Mats "TCI: Target Controlled Infusion, or Totally Confused Infusion? Call for an Optimised Population Based Pharmacokinetic Model for Propofol," Upsala J Med Sci 113(2):161-170 (2008).
Sreevastava et al. "Automated Target Controlled Infusion Systems: The Future of Total Intravenous Anaesthesia," MJAFI 64:261-262 (2008).
Casati et al. "Clinical Assessment of Target-controlled Infusion of Propofol During Monitored Anesthesia Care," Can J Anesth 46(3):235-239 (1999).
Leslie et al. "Target-controlled Infusion Versus Manually-controlled Infusion of Propofol for General Anaesthesia of Sedation in Adults," Cochrane Database of Systematic Reviews 3:1-33 (2008).
Viviand et al. "Induction and Maintenance of Intravenous Anaesthesia Using Target-controlled Infusion Systems," Best Practice & Research Clinical Anaesthesiology 15(1):19-33 (2001).
Diprifusor manual: Target Controlled Infusion (TCI) in Anaesthetic Practice, AstraZeneca pp. 1-59 (1999).
Absalom et al "Pharmacokinetic models for propofol—defining and illuminating the devil in the detail," Br J Anaesth. Jul. 2009;103(1):26-37.
Amemiya et al, "Electrochemical heparin sensing at liquid/liquid interfaces and polymeric membranes." Anal. Bioanal. Chem. 399:571-579 (2011).
Ammann et al, "Lipophilic salts as membrane additives and their influence on the properties of macro- and micro-electrodes based on neutral carriers" Analytica Chimica Acta 171 : 119-129 (1985).
Armstrong et al, "Properties of PVC based membranes used in ion-selective electrodes," Electrochim. Acta 35: 1-7(1990).
Azevedo et al. "Detection of phenol at boron-doped nanocrystalline diamond electrodes," J. Electroanal. Chem. 658:38-45 (2011).
Bard and Falkner, Electrochemical Methods, John Wiley and Sons, New York (2001).
Bhattacharya et al, "Binding of the General Anesthetics Propofol and Halothane to Human Serum Albumin," J. Biol. Chem. 275:38731-38738 (2000).
Blanco et al, "Microfluidic-optical Integrated CMOS Compatible Devices for Label-free Biochemical Sensing," J Micromechanics Microengineering 16: 1006-1016 (2006).
Bodor et al, "Electrochemical methods for the determination of the diffusion coefficient of ionophores and ionophore-ion complexes in plasticized PVC membranes," Analyst 133 :635-642 (2008).
Chen et al., "A comparison between target-controlled and manually controlled propofol infusions in patients undergoing routine surgical procedures," Eur J Anaesthesiol. Nov. 2009;26(11):928-35.
Chen et al., "The Stability of Radio-Frequency Plasma Treated Polydimethylsiloxane Surface," Langmuir 23(6):3118-3122 (2007).
Chen et al, "Computation of Transient Flow Rates in Passive Pumping Micro-fluidic Systems," Lab. Chip. 9: 107-114 (2009).
Chen and Lee, "A Bonding Technique using Hydrophilic SU-8," J Micromechanics Microengineering 17: 1978-1984 (2007).
Chen et al, "Lab-on-Chip Flow Injection Analysis System without an External Pump and Valves and Integrated with an in Line Electrochemical Detector," Anal. Chem. 81 :9955-9960 (2009).
Chen & Weber, "A high-throughput method for lipophilicity measurement," Anal. Chem. 79: 1043-1049 (2007).
Coppens et al., "Study of the time course of the clinical effect of propofol compared with the time course of the predicted effect-site concentration: Performance of three pharmacokinetic-dynamic models" Br J Anaesth. Apr. 2010;104(4):452-8.
Delamarche et al, "Stability of Molded polydimethylsiloxane," Adv. Materials 9:741-746 (1997).
Engbers et al., "Pharmacokinetic models for propofol: defining and illuminating the devil in the detail." Br J Anaesth. Feb. 2010;104(2):261-4.
Glen et al, "The Development of 'Diprifusor': A TCI System for Propofol," Anesthesia, 53,Supplement 1, pp. 13-21 (1998).
Gray et al, "Development of the Technology for 'Diprifusor' TCI Systems," Anesthesia, 53, Suppl. 1, pp. 22-27 (1998).
Grossherr et al., "Propofol concentration in exhaled air and arterial plasma in mechanically ventilated patients undergoing cardiac surgery," Br J Anaesth. May 2009;102(5):608-13.

(56) References Cited

OTHER PUBLICATIONS

Grossherr et al., "Discontinuous monitoring of propofol concentrations in expired alveolar gas and in arterial and venous plasma during artificial ventilation," Anesthesiology. Apr. 2006;104(4):786-90.

Guo et al, "Voltammetric heparin-selective electrode based on thin liquid membrane with conducting polymer-modified solid support." Anal. Chem. Oct. 1, 2006;78(19):6893-902.

Harrison et al., "Real-time breath monitoring of propofol and its volatile metabolites during surgery using a novel mass spectrometric technique: a feasibility study," Br J Anaesth. Dec. 2003;91(6):797-9.

Horvath et al, "Cyclic voltammetric experiments with plasticized PVC membranes," Anal. Chim. Acta 273: 145-152 (1993).

Kim et al., Anal. Chim. Acta 479: 143-150 (2003).

Kivlehan et al. "Toward feedback-controlled anesthesia: voltammetric measurement of propofol (2, 6-diisopropylphenol) in serum-like electrolyte solutions." Analytical chemistry 84.18 (2012): 7670-7676.

Krasowski et al., "General anesthetic potencies of a series of propofol analogs correlate with potency for potentiation of gamma-aminobutyric acid (GABA) current at the GABA(A) receptor but not with lipid solubility" J Pharmacol Exp Ther. Apr. 2001;297(1):338-51.

Langmaier et al., "Electrochemical quantification of 2,6-diisopropylphenol (propofol)", Anal Chim Acta. Oct. 17, 2011;704(1-2):63-7.

Lee and Voros, "An Aqueous-based Surface Modification of poly(dimethylsiloxane) with poly(ethylene glycol) to Prevent Biofouling," Langmuir 21 : 1 1957-11962 (2005).

Lund and Hammerich, Organic Electrochemistry, 4th Revised and Expanded Revision, Marcel Dekker, Inc, New York, 2001.

Mazzi et al., "Simple and practical high-performance liquid chromatographic assay of propofol in human blood by phenyl column chromatography with electrochemical detection," J. Chromatogr-Biomed. 528:537-541 (1990).

McDonald et al, "Fabrication of Micro fluidic Systems in poly(dimethylsiloxane)," Electrophoresis 21 :27-40 (2000).

McKeage and Perry, "Propofol: a review of its use in intensive care sedation of adults," CNS Drugs. 2003;17(4):235-72.

Miekisch et al., "Assessment of propofol concentrations in human breath and blood by means of HS-SPME-GC-MS" Clin Chim Acta. Sep. 2008;395(1-2):32-7.

Mijatovic et al, "Technologies for Nanofluidic Systems: Top-down vs. Bottom-up—A Review," Lab on a Chip 5:492-500(2005).

Mohr, "Polymer for optical sensors," Optical Chemical Sensors, vol. 224, pp. 297-321 (2006).

Nieman et al., "Neutral carrier potassium-selective electrodes with low resistances," Analytica Chimica Acta 170:359-363 (1985).

Nordstrom et al, "Rendering SU-8 Hydrophilic to Facilitate use in Micro Channel Fabrication," J Micromechanics Microengineering 14: 1614-1617 (2004).

Ruzicka & Hansen, Flow Injection Analysis, John Wiley & Sons, New York (1988).

Pissinis et al., J. Liq. Chromatogr. R. T. 30: 1787-1795 (2007).

Schnider and Minto, "Pharmacokinetic models of propofol for TCI" Anaesthesia. Feb. 2008;63(2):206.

Schywalsky et al, "Binding of Propofol to human serum albumin," Arzneimittel-Forsch. 55:303-306 (2005).

Spataru et al., "Voltammetric detection of phenol at platinum-polytyramine composite electrodes in acidic media" J. Hazard. Mater. 180:777-780 (2010).

Struys et al. "Performance evaluation of two published closed-loop control systems using bispectral index monitoring: a simulation study" Anesthesiology. Mar. 2004;100(3):640-7.

Stonell et al. "Effect-site targeted patient-controlled sedation with propofol: comparison with anaesthetist administration for colonoscopy," Anaesthesia. Mar. 2006;61(3):240-7.

Trocewicz et al, "Determination of diprivan in urine by a supported liquid membrane technique and liquid chromatography-electrochemical detection" J. Chromatogr. B. 685 :129-134 (1996).

Unger et al, "Monolithic Micro fabricated Valves and Pumps by Multilayer Soft Lithography," Science 288: 113-116(2000).

Yin et al., "Electrochemical behavior of catechol, resorcinol and hydroquinone at graphene-chitosan composite film modified glassy carbon electrode and their simultaneous determination in water samples," Electrochimica Acta 56(6)2748-2753 (2011).

Yin et al., "Voltammetric sensing of paracetamol, dopamine and 4-aminophenol at a glassy carbon electrode coated with gold nanoparticles and an organophillic layered double hydroxide," Microchimica Acta Oct. 2011, 175:39-46.

Ymeti et al, "Integration of Microfluidics with a Four-channel Integrated Optical Young Interferometer Immunosensor," Biosens. Bioelectron. 20: 1417-1421 (2005).

Zaccheo and Bucher, "Propofol infusion syndrome: a rare complication with potentially fatal results" Crit Care Nurse. Jun. 2008;28(3):18-26.

Zejli et al., "Phenol biosensor based on Sonogel-Carbon transducer with tyrosinase alumina sol-gel immobilization," Anal Chim Acta Apr. 7, 2008;612(2):198-203.

CA Office Action dated Oct. 14, 2016; CA 2,740,421.

CA Office Action dated Dec. 4, 2015; CA 2,740,421.

EP Search report dated Jun. 20, 2017 (EP 13 798 117.1).

Phillips et al. "Measurement of sodium ion concentration in undiluted urine with cation-selective polymeric membrane electrodes after the removal of interfering compounds" Talanta. Nov. 30, 2007; 74(2): 255-264.

* cited by examiner

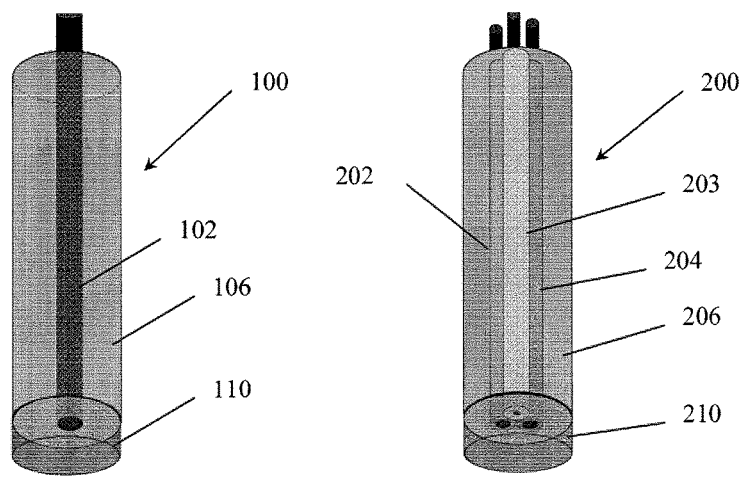
*FIG. 1*          *FIG. 2*

METHOD AND DEVICE FOR DETECTION OF BIOAVAILABLE DRUG CONCENTRATION

This application is a national stage application under 35 U.S.C. § 371 from PCT Application No. PCT/US2013/031747, filed Mar. 14, 2013, which claims the priority benefit of U.S. Provisional Patent Application Ser. No. 61/654,469, filed Jun. 1, 2012, which is hereby incorporated by reference in its entirety.

The present invention was made with support from the United States Army, Medical Research and Material Command under grants W81XWH-05-2-0064 and W81XWH-10-1-0358. The government has certain rights in this invention.

FIELD OF THE INVENTION

The present invention relates to an improved method and device for detection of bioavailable drug concentration.

BACKGROUND OF THE INVENTION

The intravenous drug 2,6-diisopropylphenol (propofol) is a proven general anesthetic which is widely used in many surgical and critical care settings for the purpose of general anesthesia or conscious sedation (Krasowski et al., *J Pharm Exp Therap* 297:338-351 (2001)). The broad appeal and popularity of propofol is related to the rapid induction and rapid elapse of anesthesia. The target steady-state concentration range of propofol in blood is between 0.25-2.0 µg/mL or 1-12 µM. In general, these target values are set by constant infusion rates ranging between 0.3-3.0 mg/kg/h.

Propofol infusion syndrome (PRIS) is a well-known adverse event that is associated with high doses and long term use of propofol (Zaccheo et al., *Crit Care Nurse* 28:18-25 (2008); McKeage and Perry, *CNS Drugs* 17:235-272 (2003)). It can lead to cardiac and renal failure in critically ill patients and is often fatal. Successful treatment of PRIS requires early recognition and immediate discontinuation of propofol infusion. The propofol related death of Michael Jackson has recently brought the safety of propofol administration into the limelight and underlined the importance of monitoring propofol during anesthesia.

Target-controlled infusion anesthesia (TCIA) aims to provide stable, user-defined, blood concentrations of anesthetic drugs using small-platform delivery systems. The infusion rate of the drug is set by algorithms utilizing population-based pharmacokinetic data and individual patient biometrics (Schnider and Minto, *Anaesthesia* 63:206 (2008); Coppens et al., *Brit J Anaesth* 104:452-458 (2010); Struys et al., *Anesthesiology* 100:640-647 (2004); Stonell et al., *Anaesthesia* 61:240-247 (2006); Absalom et al., *Brit J Anaesth* 103:26-37 (2009); Absalom et al., *Brit J Anaesth* 104:261-264 (2010)). TCIA of propofol is now widely used outside of North America. However, the U.S. Food and Drug Administration (FDA) has not approved TCIA for use in the United States despite numerous studies that have documented excellent patient safety profiles for various forms of anesthesia using this approach (Casati et al., *Can J Anaesth* 46:235-239 (1999); Chen et al., *Eur J Anesth* 26:928-935 (2009); Leslie et al., *Cochrane Db Syst Rev* (2008)). Measuring propofol levels in real-time during anesthesia and correlating blood levels with efficacy data would greatly enhance the safety of propofol delivery and potentially permit the approval of "closed-loop TCIA". To date, real-time measurements of propofol concentration in blood and other biological fluids have been elusive. Instead, most of the efforts are focused on monitoring propofol in the exhaled breath (Grossherr et al., *Brit J Anaesth* 102:608-613 (2009); Harrison et al., *Brit J Anaesth* 91:797-799 (2003); Grossherr et al., *Anesthesiology* 104:786-790 (2006); Miekisch et al., *Clin Chim Acta* 395:32-37 (2008)) and finding the correlation between the exhaled breath and plasma values (Grossherr et al., *Anesthesiology* 104:786-790 (2006).

The difficulties for electrochemical quantification of propofol in aqueous solution have been discussed in the literature (Langmaier et al., *Anal. Chim. Acta* 704:63-67 (2011)). While propofol can be oxidized electrochemically, similar to other phenolic compounds (Azevedo et al., *J. Electroanal. Chem.* 658:38-45 (2011); Kim et al., *Anal. Chim. Acta* 479:143-150 (2003); Spataru et al., *J. Hazard. Mater.* 180:777-780 (2010); Yin et al., *Microchim. Acta* 175:39-46 (2011); Yin et al., *Electrochim. Acta* 56:2748-2753 (2011); Zejli et al., *Anal. Chim. Acta* 612:198-203 (2008)), product(s) from the electrochemical oxidation and coupled reactions may deposit to the electrode surface causing immediate passivation or gradual electrode fouling. Although the detrimental effect of electrode fouling could be minimized, the previously reported detection limit (3.2 µM) and selectivity remained inadequate for monitoring propofol in biological samples. Due to the limited selectivity of voltammetric methods, electrochemical propofol sensors are mainly used as detectors in chromatographic separation (Mazzi et al., *J. Chromatogr-Biomed.* 528:537-541 (1990); Pissinis et al., *J. Liq. Chromatogr. R. T* 30:1787-1795 (2007); Trocewicz et al., *J. Chromatogr. B.* 685:129-134 (1996)). It is therefore desirable to identify an improved electrochemical sensor that can detect propofol as well as other electrochemically active drugs or metabolites in biological samples across their physiological and therapeutic ranges.

The present invention is directed to overcoming these and other deficiencies in the art.

SUMMARY OF THE INVENTION

A first aspect of the present invention relates to an electrochemical sensor including an electrode and a coating that surrounds the electrode, the coating comprising a structural component, a water immiscible solvent, a resistance decreasing component, and an ion exchange component, wherein the coating selectively partitions an electrochemically active drug from a fluid or vapor sample whereby an electrochemical signal within the coating can be measured using the electrode.

A second aspect of the present invention relates to a target-controlled infusion drug delivery device that includes a drug reservoir, a pump in communication with the drug reservoir, an electrochemical sensor according to the first aspect of the present invention, and a control system that receives an output of the electrochemical sensor upon detection of the bioavailable drug concentration in a fluid or vapor sample and controls operation of the pump based on the detected concentration of bioavailable drug.

A third aspect of the present invention relates to a microfluidic device that includes a microfluid channel and an electrochemical sensor according to the first aspect of the present invention in communication with the microfluid channel.

A fourth aspect of the present invention relates to a method of modulating drug delivery that includes exposing a fluid or vapor sample obtained from a patient to an electrochemical sensor according to the first aspect of the present invention; detecting an electrochemical signal within the coating during said exposing, wherein the detected electrochemical signal relates to a concentration of bioavailable drug in the fluid or vapor sample; and modulating delivery of the drug into a patient based on the concentration of the bioavailable drug in the fluid or vapor sample.

A fifth aspect of the present invention relates to a method for electrochemical detection of bioavailable drug concentration in a fluid or vapor sample, which method includes exposing a fluid or vapor sample to an electrochemical sensor according to the first aspect of the present invention; and detecting an electrochemical signal within the coating during said exposing, wherein the detected electrochemical signal relates to the concentration of bioavailable drug in the fluid or vapor sample.

The accompanying experimental data demonstrate the preparation and testing of electrochemical sensors that permit electrochemical monitoring of propofol in aqueous electrolyte solutions, blood, serum, or plasma. This will allow for the construction of a closed-loop, feedback controlled infusion of propofol during anesthesia. To obtain a mechanically robust working electrode, the organic film was immobilized to the electrode surface in the form of a highly plasticized PVC membrane (Horvath et al., *Anal. Chim. Acta* 273:145-152 (1993); Amemiya et al., *Anal. Bioanal. Chem.* 399:571-579 (2011); Guo et al., *Anal. Chem.* 78:6893-6902 (2006), each of which is hereby incorporated by reference in its entirety). Coating the surface of a working electrode, advantageously made of glassy carbon or gold, with a highly plasticized PVC membrane prevented electrode fouling and allowed for chronoamperometric detection of sub-micromolar levels of propofol in serum-like electrolytes containing 5% bovine serum albumin (BSA), 3 mM ascorbic acid (AA), and 1 mM p-acetamido phenol (APAP), as well as in serum like electrolytes containing 5% human serum albumin (HSA), 3 mM ascorbic acid (AA), and 1 mM p-acetamido phenol (APAP), and patient serum samples.

BRIEF DESCRIPTION OF THE DRAWINGS

FIG. 1 shows a three dimensional representation of a single macroelectrode, where the electrode (e.g., carbon, gold, or platinum) is incorporated into an insulating matrix, e.g., glass, and the surface of the electrode is covered by a film or coating that is capable of partitioning the bioavailable drug from the sample.

FIG. 2 shows a three dimensional representation of an electrochemical cell containing three electrodes (working, counter, and reference electrodes), where the surface of the entire electrochemical cell is coated with a film or coating that is capable of partitioning the bioavailable drug from the sample.

FIG. 17 confirms that the 5% BSA containing standards can be used to assess the concentration in human serum samples.

DETAILED DESCRIPTION OF THE INVENTION

Figure 3:
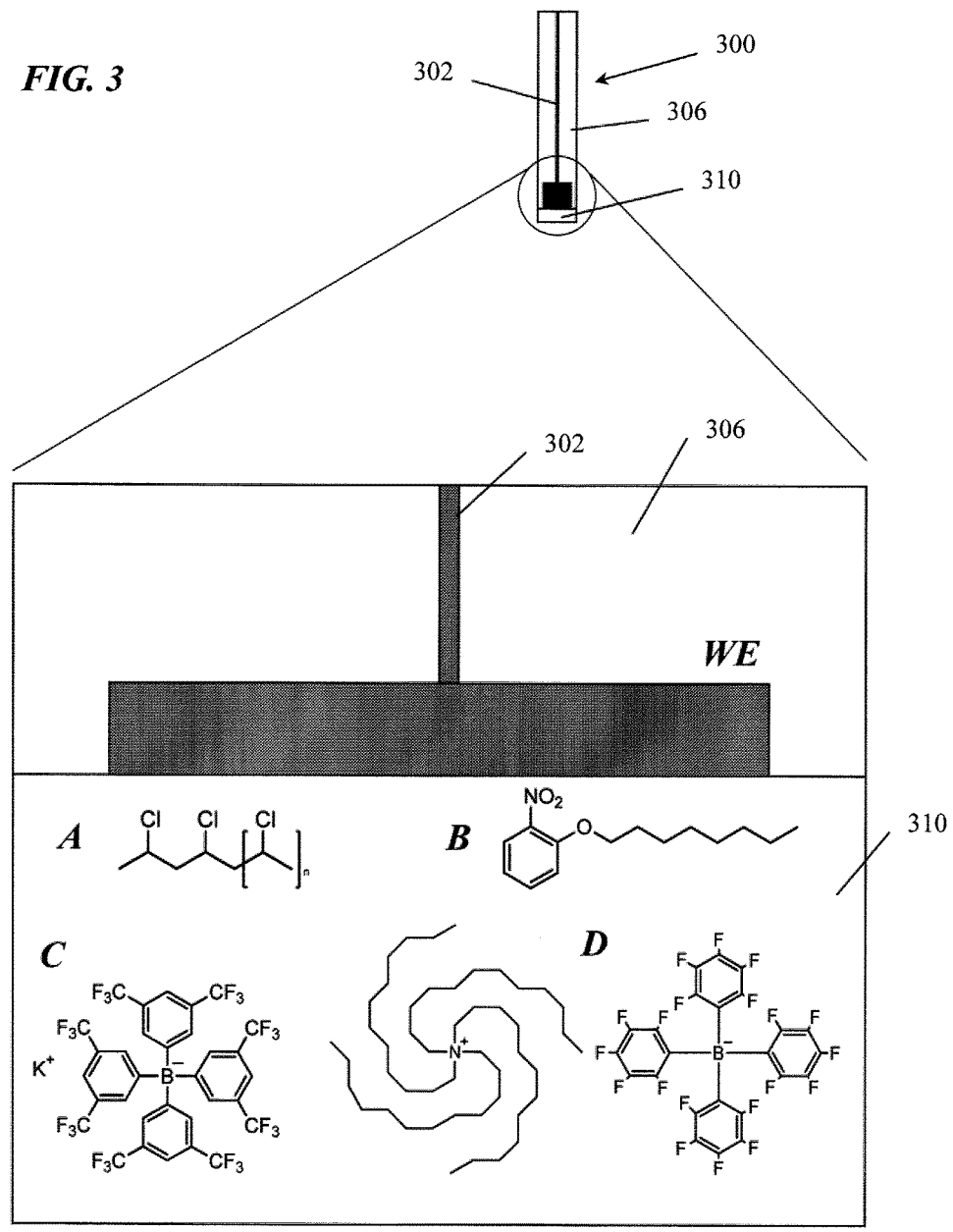
FIG. 3 shows a macroelectrode with the surface of the embedded carbon or metal disc-shaped working electrode (WE) covered by a film or coating that is capable of partitioning the bioavailable drug from the sample. In the enlarged portion of the Figure, the WE surface and coating are schematically illustrated. The graphite or metal working electrode (WE) material is embedded in an insulator matrix. The coating includes A, chemical representation of PVC, which is an example of the structural component of the membrane; B, chemical representation of 2-nitrophenyl octyl ether, an example of the water immiscible organic solvent of the membrane; C, chemical representation of potassium tetrakis[3,5,bis(trifluoromethyl)phenyl]borate as an exemplary ion exchange component of the membrane; and D, chemical representation of the exemplary resistance controlling component tetradodecylammonium tetrakis(pentafluorophenyl)borate.

The present invention relates to electrochemical sensors for the detection of total or bioavailable drug concentration, and devices and methods that include or utilize the electrochemical sensors for control over the delivery of a drug based on the total or bioavailable drug concentration. In preferred embodiments, delivery of a drug is adjusted, if necessary, in real time following a sensing event.

As used herein, the term "real-time" is intended to mean a response that is carried out within less than about a minute, preferably less than about 20 or 10 seconds, and most preferably within about 1 to about 5 seconds following a detection event.

As used herein, the term "fluid sample" is intended to mean a body fluid sample including, without limitation blood, plasma, cerebrospinal fluid, and other body fluids. The body fluid sample may be diluted with, e.g., buffer or other reagents that facilitate handling. As used herein, the term "vapor sample" is intended to mean a sample containing a non-liquid component and optionally entrained liquid component. A preferred vapor sample is exhaled breath, which may be diluted with additional gas prior to detection or concentrated by removing certain components of the vapor sample. Both fluid samples and vapor samples can be used to detect the drug or metabolite concentration. As used herein, the term "sample" without further description is intended to encompass both fluid samples and vapor samples.

As used herein, the term "bioavailable drug concentration" is intended to mean the concentration of a drug that exists free in a fluid sample, or the drug that exists in a vapor sample. As used herein, the term "total drug concentration" includes the sum of the bioavailable drug concentration and the concentration of drug that is complexed, e.g., bound to plasma proteins. In some embodiments, the bioavailable drug concentration may be the same as or similar to the total drug concentration (i.e., little if any of the drug is bound). In other embodiments, the total drug concentration may be detectable to the extent that the drug is adequately partitioned into the sensor coating of the present invention regardless of its status as bioavailable. Any of a variety of electrochemically active drugs or metabolites can be monitored in accordance with the present invention, particularly drugs, therapeutic agents, or metabolites that are hydrophobic, polar, or amphiphilic. Exemplary classes of drugs, therapeutic agents, or metabolites include, without limitation, antibiotics, antifungals, antivirals, antihypertensives, antiemetics, narcotics, antimetabolites, anxiolytics, chemotherapeutics, anticoagulants, vitamins, anesthetics, barbiturates, and sedatives. Preferred drugs that are hydrophobic, polar, or amphiphilic, and therefore can be detected in accordance with the present invention include, without limitation, propofol, midazolam, methohexitol, etomidate and sufentanol.

By way of example, propofol is a highly lipophilic compound with reported log P values between 3.83 (see Drugs.com Internet site (2012)) and 4.15 (Krasowski et al., *J. Pharm. Exp. Therap.* 297:338-351 (2001), which is hereby incorporated by reference in its entirety), where P is the octanol/water partition coefficient. The high lipophilicity of propofol offers an opportunity to enhance the voltammetric signal by using an organic-film modified working electrode. Due to its high lipophilicity, the concentration of propofol should be orders of magnitude higher in the film than in the aqueous sample. Other electrochemically active drugs or metabolites having log P values greater than −2.0 can be detected, including those identified above. In certain embodiments, the electrochemically active drugs or metabolites have a log P value that is greater than 2.0.

Accordingly, a first aspect of the present invention relates to an electrochemical sensor or sensor array that can be used to detect bioavailable drug concentration from a fluid or vapor sample.

The electrochemical sensor includes an electrode and a coating that surrounds the electrode, the coating comprising a structural component, a water immiscible solvent, a resistance decreasing component, and an ion exchange component, wherein the coating selectively partitions an electrochemically active drug from a fluid or vapor sample whereby an electrochemical signal within the coating can be measured using the electrode.

The sensor design and the electrochemical signal that is detected by the sensor can be according to any of a variety of known sensor formats, including without limitation a chronoamperometric sensor (measuring current as the function of time as the signal), voltammetric sensor (measuring current as the function of the applied voltage as a signal), a potentiometric sensor (measuring the phase boundary potential as the signal), a conductometric sensor (measuring resistance or conductance as the signal), or a coulometric sensor (measuring charge as the signal).

The minimum number of electrodes used for each of these sensor designs is well known in the art. A voltammetric sensor can include, without limitation, one or more working electrodes in combination with a reference electrode, or one or more working electrodes in combination with a reference electrode and a counter electrode. In voltammetry, different potential programs can be applied to the working electrode, e.g., the potential can be varied over time (linear sweep voltammetry or cyclic voltammetry), potential can also be constant (chronoamperometry) or applied as pulses with the same or changing amplitude (pulse voltammetric methods) to measure the current related to the analyte concentration with the membrane coated sensor. A chronoamperometric sensor typically utilizes one or more working electrodes in combination with a reference electrode and a counter electrode, and the potential applied to the working electrode is constant or is applied as short pulses to measure the current related to the oxidation or reduction of the analyte with the membrane coated sensor. Chronoamperometry typically yields a better signal to noise ratio in comparison to other amperometric techniques. A conductometric sensor can include two or four electrodes, which measure the impedance of the coating with the sample solution. A potentiometric cell can include two electrodes, in which the potential of the indicator electrode is measured at zero current. A coulometric sensor can include two or more electrodes and measures the charge related to the oxidation or reduction of the analyte in the membrane coating. The design and principles surrounding these types of electrochemical sensors are described in Bard and Falkner, *Electrochemical Methods*, John Wiley and Sons, New York (2001); and Toth et al., "Electrochemical Detection in liquid Flow Analytical Techniques: Characterization and Classification," *Pure Appl. Chem.* 76(6):1119-1138 (2004), each of which is hereby incorporated by reference in its entirety.

Reference electrodes, counter or auxiliary electrodes, and the working electrode can be formed out of a suitable conductive material including, without limitation, carbon, silver, mercury, gold, platinum, palladium, ruthenium, rhodium or combinations thereof. The particular function and number of electrodes will depend upon the type of electrochemical sensor that is employed, and aspects of the present invention are not limited by specific formation(s) of the electrochemical sensor illustrated below. At least the working electrode is covered by the coating.

Three dimensional representations of a single macroelectrodes where the one or more electrodes (e.g., carbon, gold, or platinum) is incorporated into an insulating matrix, e.g., glass, and the surface of the electrode or the surface of the entire electrochemical cell is coated with a film or coating that is capable of partitioning the bioavailable drug from the sample are shown in FIGS. 1 and 2. In FIG. 1, macroelectrode 100 contains a single electrode 102 encapsulated by glass matrix 106, and the surface of the electrode is shown embedded in the film or coating 110. In FIG. 2, electrochemical cell 200 containing three electrodes (working, 202; counter, 203; and reference, 204; electrodes) encapsulated by glass matrix 206, and the surfaces of the electrodes are shown embedded in the film or coating 210.

The film or coating that covers at least one electrode preferably includes a structural component, water immiscible solvent (or plasticizer), a resistance decreasing component, and an ion exchange component. The coating may optionally contain one or more further additives including, without limitation, adhesion enhancing and biocompatibility enhancing component, as well as any additional agents that inhibit certain biological responses, such as anti-inflammatory agents, anticoagulants, etc.

Any suitable structural component can be utilized in the coating. The structural component can be polymeric or non-polymeric. Exemplary structural components include, without limitation, porous carbon materials as well as polymeric materials selected from the group of polyvinylchloride (PVC), silicone rubber, polyurethane, (meth)acrylate polymer, polypyrrole, polythiophene, polyoctylthiophene, polyanaline, polyvinyl pyrrolidone, agarose, hydrogel, sol-gel materials, and combinations thereof. In certain embodiments, the structural component can form a relatively minor portion of the coating, and in other embodiments the structural component can form a major portion of the coating.

The structural component is preferably present in an amount of about 5 to about 80 wt. percent of the total coating, more preferably about 15 to about 70 wt. percent of total coating. In certain embodiments, the structural component is present in an amount of about 20 to 30 wt. percent of the total coating. In alternative embodiments, the structural component is present in an amount of about 30 to 50 wt. percent of the total coating. In certain embodiments, the structural component can also serve as working electrode, e.g., porous three dimensional carbon materials.

Any suitable water immiscible organic solvent (or plasticizer) can be utilized in the coating. The organic solvent is responsible for assisting in the partitioning of the bioavailable drug from the fluid sample into the coating. Exemplary water immiscible organic solvents include, without limitation, 2-nitrophenyl octyl ether (o-NPOE), dioctyl sebacate (DOS), bis(2-ethylhexyl) sebacate, benzyl 2-nitrophenyl ether, bis(1-butylpentyl) adipate, bis(2-ethylhexyl) adipate, bis(2-ethylhexyl) phthalate, 1-chloronaphthalene, chloroparaffin, 1-octanol, 1-decanol, dibutyl phthalate, dibutyl sebacate, dibutyl-dilaurate, dodecyl 2-nitrophenyl ether, and combinations thereof. In certain embodiments the organic solvent can be a fluorinated liquid, e.g. without limitation perfluorooctane, perfluorononane, perfluoro(2-methyloctane), perfluorodecaline and combinations thereof. In certain embodiments where the structural component forms a minor portion of the coating, then the organic solvent can form a relatively major portion of the coating; and in other embodiments where the structural component form a major portion of the coating, then the organic solvent can form a relatively minor portion of the coating.

The organic solvent is preferably present in an amount of about 5 to about 85 wt. percent of the total coating, more preferably about 10 to about 70 wt. percent of total coating. In certain embodiments, the organic solvent is present in an amount of about 45 to about 55 wt. percent of the total coating. In one alternative embodiment, the structural component is present in an amount of about 30 to 45 wt. percent of the total coating. In another alternative embodiment, the structural component is present in an amount of about 55 to about 70 wt. percent of the total coating.

The resistance decreasing component is an organic salt that is not soluble in water and includes both a lipophilic cation and a lipophilic anion. As used herein, an organic salt that is not soluble is one that is characterized by a log P value (indeed the logarithm of the membrane water partition coefficient) that is larger than 6.1 or log D value (membrane distribution coefficient) that is larger than 6.1 at the sample solution pH at which the analysis is performed. Considered in terms of the amount of organic salt lost from the membrane to an aqueous sample solution, for two hours of monitoring the amount of organic salt lost from the membrane is about 1% of the starting amount.

The lipophilic cation is preferably an ammonium cation or phosphonium cation, more preferably a quaternary ammonium cation or a tetraarylphosphonium cation. The quaternary ammonium cations are preferably tetraalkylammonium cations where the alkyl groups are independently 1 to 48, preferably 4 to 24, carbon atoms.

Exemplary lipophilic cations include, without limitation, tetradodecylammonium, tetraphenylphosphonium, bis(triphenylphosphoranylidine) ammonium, dimethyldioctadecyl ammonium, hexadecyltrioctadecylammonium, methyltrioctadecylammonium, tetrahexadecylammonium, tetraoctadecylammonium, tetraoctylammonium, tridodecylmethylammonium, tris[(perfluorooctyl)propyl]ammonium, and combinations thereof.

The lipophilic anion is preferably a borate, sulfonate, or a carborane, including halogenated or nonhalogenated carboranes. Of these, borates and sulfonates are preferred.

Exemplary lipophilic anions include, without limitation, tetraphenylborate, tetrakis(pentafluorophenyl)borate, tetrakis(4-chlorophenyl)borate, tetrakis[3,5,bis(trifluoromethyl)phenyl]borate, tetrakis(4-fluorophenyl)borate, dinonylnaphthalene sulphonate, tetrakis[3,5-bis(perfluorohexyl)phenyl]borate, tetrakis(p-tolyl)borate, tetrakis(m-tolyl)borate, tetrakis(2,4-dimethyl)borate, tetrakis(3,5-dimethylphenyl)borate, closo-dodecacarborane, undecachlorinated carborane (UCC), hexabrominated carborane (HBC), undecaiodinated carborane (UIC), undecabromocarborane, and combinations thereof.

Thus, exemplary water insoluble organic salts of the invention include, without limitation: tetradodecylammonium tetrakis(pentafluorophenyl) borate (TDDATPFPhB), bis(triphenylphosphoranylidene)ammonium tetrakis[3,5,bis(trifluoromethyl)phenyl]borate (BTPPATFPhB), tetradodecylammonium tetrakis(4-chlorophenyl)borate, tris[(perfluorooctyl)propyl]ammonium tetrakis[3,5-bis(perfluorohexyl)phenyl]borate, tetraheptylammonium tetraphenylborate, tetradodecylammonium dinonylnaphthalene sulphonate, tetraphenylphosphonium tetraphenylborate, tetraphenylphosphonium tetrakis(pentafluorophenyl)borate, tetraphenylphosphonium tetra-p-tolylborate, tetraphenylphosphonium tetra-m-tolylborate, bis(triphenylphosphoranylidene)ammonium tetraphenylborate, bis(triphenylphosphoranylidene)ammonium tetrakis(pentafluorophenyl)borate, bis(triphenylphosphoranylidene)ammonium tetrakis(4-chlorophenyl)borate, bis(triphenylphosphoranylidene)ammonium tetrakis[3,5,bis(trifluoromethyl)phenyl]borate, bis(triphenylphosphoranylidene)ammonium tetrakis(4-fluorophenyl)borate, hexadecyltrioctadecylammonium tetraphenylborate, tetraoctadecylammonium tetraphenylborate, tetraoctadecylammonium tetrakis(4-chlorophenyl)borate, tetraoctadecylammonium tetraphenylborate, tetraoctadecylammonium tetrakis(4-chlorophenyl)borate, tetraoctadecylammonium tetrakis(4-fluorophenyl)borate, tetraoctylammonium tetraphenylborate, tetraoctylammonium tetrakis(pentafluorophenyl)borate, tetraoctylammonium tetrakis(4-chlorophenyl)borate, tetraoctylammonium tetrakis[3,5,bis(trifluoromethyl)phenyl]borate, tetraoctylammonium tetrakis(4-fluorophenyl)borate, tridodecylmethylammonium tetraphenylborate, tridodecylmethylammonium tetrakis(pentafluorophenyl)borate, tridodecylmethylammonium tetrakis(4-chlorophenyl)borate, tridodecylmethylammonium tetrakis[3,5,bis(trifluoromethyl)phenyl]borate, tridodecylmethylammonium tetrakis(4-fluorophenyl)borate, tridodecylmethylammonium dinonylnaphthalene sulphonate, dodecyltrimethylammonium dinonylnaphthalene sulphonate, tetrabutylammonium tetraphenylborate, tetrabutylammonium tetrakis(pentafluorophenyl)borate, tetrabutylammonium tetrakis(4-chlorophenyl)borate, tetrabutylammonium tetrakis(4-fluorophenyl)borate, tetrabutylammonium tetrakis[3,5,bis(trifluoromethyl)phenyl]borate, tetraphenylphosphonium tetraphenylborate, trimethylammonium undecabromocarborane (TMAUBC), and combinations thereof.

The resistance decreasing component is preferably present in an amount of about 1 to about 30 wt. percent of the total coating, more preferably about 5 to about 25 wt. percent of the total coating. In certain embodiments, the resistance decreasing component is present in an amount of about 5 to 10 wt. percent of the total coating. In alternative embodiments, the resistance decreasing component is present in an amount of about 10 to 20 wt. percent of the total coating. In a further embodiment, the resistance decreasing component is present in an amount of about 20 to about 25 wt. percent of the total coating.

The ion exchange component is either (i) a cation exchanger that includes a hydrophilic cation and a lipophilic anion, or (ii) an anion exchanger that includes a lipophilic cation and a hydrophilic anion.

The hydrophilic cation of the cation exchanger can be any water soluble cation. Exemplary hydrophilic cations include, without limitation, those selected from the group of alkali metal (e.g., lithium, sodium, potassium) cations, alkaline earth metal (e.g., magnesium, calcium) cations, transition metal (e.g., manganese, iron, zinc) cations, and complex (e.g., ammonium) cations.

The lipophilic anion of the cation exchanger can be any of the water insoluble borates, sulfonates, and halogenated and nonhalogenated carboranes as identified above for the resistance decreasing component.

Exemplary cation exchangers include, without limitation, sodium or potassium tetrakis[3,5bis(trifluoromethyl)phenyl]borate (NaTFPhB or KTFPhB), sodium or potassium tetrakis[pentafluorophenyl]borate (NaTPFPhB or KTPFPhB), sodium or potassium tetrakis(4-chlorophenyl) borate (NaTpClPhB or KTpClPhB), sodium or potassium tetraphenylborate, sodium or potassium tetrakis(4-fluorophenyl)borate, sodium or potassium tetrakis(p-tolyl)borate, sodium or potassium tetrakis(m-tolyl)borate, sodium or potassium tetrakis(2,4-dimethyl)borate, sodium or potassium tetrakis(3,5-dimethylphenyl)borate, sodium or potassium tetrakis[3,5-bis(1,1,1,3,3,3-hexafluoro-2-methoxy-2-propyl)phenyl]borate, sodium or potassium tetrakis[3,5-bis(perfluorohexyl)phenyl]borate, sodium or potassium tetrakis[3,5bis(trifluoromethyl)phenyl]aluminate, sodium or potassium tetrakis[pentafluorophenyl]aluminate, sodium or potassium tetrakis(4-chlorophenyl)aluminate, sodium or potassium tetraphenylaluminate, sodium or potassium tetrakis(4-fluorophenyl)aluminate, sodium or potassium tetrakis(p-tolyl)aluminate, sodium or potassium tetrakis(m-tolyl)aluminate, sodium or potassium tetrakis(2,4-dimethyl)aluminate, sodium or potassium tetrakis(3,5-dimethylphenyl)aluminate, and combinations thereof.

The lipophilic cation of the anion exchanger can be any of the water insoluble cations identified above for the for the resistance decreasing component, preferably the quaternary ammonium cations, bis(triphenylphosphoranylidene) ammonium cations, tris[(perfluorooctyl)propyl]ammonium cations, and tetraarylphosphonium cations identified above.

The hydrophilic anion of the anion exchanger can be any water soluble anion. Exemplary anions include, without limitation, those selected from the group of halides (e.g., F$^-$, Cl$^-$, Br$^-$, I$^-$), NO$_3^-$, SO$_4^{2-}$, SO$_3^{2-}$, HSO$_3^-$, CO$_3^{2-}$, HCO$_3^-$, HPO$_4^{2-}$, H$_2$PO$_4^-$, and ClO$_4^-$.

Exemplary anion exchangers include, without limitation, a quaternary ammonium chlorides, bromides, or perchlorates, and bis(triphenylphosphoranylidene) ammonium chlorides or bromides.

The ion exchange component is preferably present in an amount of about 0.001 to about 30 wt. percent of the total coating, more preferably about 0.5 to about 25 wt. percent of total coating, more preferably about 0.5 to about 5 wt. percent. In certain embodiments, the ion exchange component is present in an amount of about 0.5 to 10 wt. percent of the total coating. In alternative embodiments, the ion exchange component is present in an amount of about 10 to 20 wt. percent of the total coating. In a further embodiment, the ion exchange component is present in an amount of about 20 to about 30 wt. percent of the total coating.

In certain embodiments of the present invention, the coating includes about 5 to about 80 wt. percent of the structural component, about 5 to about 85 wt. percent of the water immiscible solvent, about 5 to about 30 wt. percent of the resistance decreasing component, and about 0.001 to about 30 wt. percent of the ion exchange component.

In another embodiment of the present invention, the coating includes about 15 to about 70 wt. percent of the structural component, about 10 to about 70 wt. percent of the water immiscible solvent, about 5 to about 30 wt. percent of the resistance decreasing component, and about 0.5 to about 5 wt. percent of the ion exchange component.

In certain exemplary embodiments, the coating includes about 20 to 30 wt. percent of PVC as the structural component; about 45 to 55 wt. percent of o-NPOE, DOS, or 1-octanol as the water immiscible solvent; about 20 to 25 wt. percent of TDDATPFPhB or BTPPATFPhB as the resistance decreasing component; and about 2 to about 4 wt. percent of NaTFPhB or KTPFPhB as the ion exchanger component.

Any suitable adhesion enhancing component can be utilized in the coating, when desired for preventing the formation of an aqueous layer between the coating and the working electrode surface or between the coating and the planar electrochemical cell surface.

Any suitable biocompatibility enhancing component can be utilized in the coating, when desired. Exemplary biocompatibility enhancing components include, without limitation, nitric-oxide releasing sol-gel materials, N-(6-aminohexyl) aminopropyltrimethoxysilane, balanced isobutyltrimethoxysilane diazeniumdiolate, and combinations thereof. These can be used in amounts up to about 5 wt. percent, preferably between about 0.001 to about 3 wt. percent.

Any suitable anti-inflammatory agents can be utilized in the coating, when desired. These can be used in amounts up to about 5 wt. percent, preferably between about 0.001 to about 3 wt. percent. These agents should not interfere with the electrochemical signal caused by partitioning of the drug into the coating.

Any suitable anti-coagulant agents can be utilized in the coating, when desired. These can be used in amounts up to about 5 wt. percent, preferably between about 0.001 to about 3 wt. percent. These agents should not interfere with the electrochemical signal caused by partitioning of the drug into the coating.

The coating can be of any suitable dimension that affords effective partitioning while allowing for sufficient electrochemical signaling within coating. For example, and not by limitation, in certain embodiments the coating is less than about 200 μm thick, more preferably less than about 100 μm thick. According to one embodiment, the coating is between about 1 to about 25 μm thick. According to another embodiment, the coating has a sub-micron thickness.

Application of the coating over the electrode can be carried out by first forming a mixture of the component ingredients, which are dissolved in a suitable solvent such as THF, and then applying the dissolved solution using any of a variety of means including, without limitation, spray-coating, spin-coating, dip-coating, roller-coating, blade-coating, etc. The particular choice of coating technique will depend on its compatibility with the structure of the electrochemical cell that forms part of the sensing device of the present invention. During and subsequent to application the solvent used to disperse the components is removed, leaving the coating applied to a surface of the electrode(s).

By way of example, one embodiment of the electrochemical sensor is illustrated in FIG. 3. In this figure, a macroelectrode 300 encapsulated in glass matrix 306 is shown with the surface of the single, embedded carbon or metal disc-shaped working electrode (WE) 302 embedded in the coating 310. In the enlarged portion of this figure, the WE surface and coating are schematically illustrated. The graphite or metal working electrode (WE) material embedded in an insulator matrix. The coating components include: A, chemical representation of PVC, which is an example of the structural component of the membrane; B, chemical representation of 2-nitrophenyl octyl ether, the water immiscible organic solvent of the membrane; C, chemical representation of the ion exchange component potassium tetrakis[3,5, bis(trifluoromethyl)phenyl]borate; and D, chemical representation of the resistance controlling component tetradodecylammonium tetrakis(pentafluorophenyl)borate.

As demonstrated in the accompanying examples, electrochemical sensors of the present invention are capable of detecting propofol levels in a fluid sample which are well below the therapeutic target steady state concentration for blood/serum levels thereof. In particular, the lower limit of detection for propofol is shown to be at submicromolar concentrations, which is about 1-2 orders of magnitude below the therapeutic range for this drug.

A further embodiment is a microfluidic sensor that includes one or more electrochemical sensors of the invention in communication with a microfluidic channel through which the fluid sample passes during the detection procedure. The coated electrodes are positioned with their coating in communication with the microfluidic channel through which the fluid sample passes during the detection procedure.

Regardless of the format of the planar electrochemical cell, microfluidic devices are preferably fabricated from materials that are biocompatible and resistant to biofouling. Several existing materials, widely used for the fabrication of fluidic channels, can address these basic needs. Two categories can be distinguished among them: those based on glasses, such as glass, Pyrex, quartz, etc. (Ymeti et al., "Integration of Microfluidics with a Four-channel Integrated Optical Young Interferometer Immunosensor," *Biosens. Bioelectron.* 20:1417-1421 (2005), which is hereby incorporated by reference in its entirety); and those based on polymers such as polyimide, photoresist, SU-8 negative photoresist, PDMS, and silicone elastomer PDMS (McDonald et al., "Fabrication of Microfluidic Systems in poly (dimethylsiloxane)," *Electrophoresis* 21:27-40 (2000), which is hereby incorporated by reference in its entirety), liquid crystal polymer, Teflon, etc. While the glass materials have great chemical and mechanical resiliency, their high cost and delicate processing make them less frequently used for this kind of application. In contrast, polymers have gained wide acceptance as the materials of choice for fluidics applications. Moreover, structuring technologies involved in their use, such as bonding, molding, embossing, melt processing, and imprinting technologies, are now well developed (Mijatovic et al., "Technologies for Nanofluidic Systems: Top-down vs. Bottom-up—A Review," *Lab on a Chip* 5:492-500 (2005), which is hereby incorporated by reference in its entirety). An additional advantage of polymer-based microfluidic systems is that valves and pumps made with the same material are readily integrated (Unger et al., "Monolithic Microfabricated Valves and Pumps by Multilayer Soft Lithography," *Science* 288:113-116 (2000), which is Hereby incorporated by reference in its entirety).

PDMS and SU-8 resist are particularly well studied as raw materials for the construction of microfluidic systems. Their mechanical and chemical comportment are strongly disparate: SU-8 is stiffer (Blanco et al., "Microfluidic-optical Integrated CMOS Compatible Devices for Label-free Biochemical Sensing," *J Micromechanics Microengineering* 16:1006-1016 (2006), which is hereby incorporated by reference in its entirety) than PDMS, and so the structuring techniques of these two materials are different. PDMS is also subject to wall collapse, depending on the aspect ratios of the channels (Delamarche et al., "Stability of Molded polydimethylsiloxane," *Adv. Materials* 9:741-746 (1997), which is hereby incorporated by reference in its entirety). Their chemical properties are an important aspect for the wanted application. They both have a hydrophobic surface after polymerization, which can lead to an attachment of the proteins onto the PDMS walls, and can fill the channel in case of small cross-section. Both the surface of PDMS and of SU-8 can be treated with a surfactant or by plasma or UV-irradiation to render the surface hydrophilic (Nordstrom et al., "Rendering SU-8 Hydrophilic to Facilitate use in Micro Channel Fabrication," *J Micromechanics Microengineering* 14:1614-1617 (2004); Chen et al., "Stabilization of the Hydrophilicity of Radio-Frequency Plasma Treated Polydimethylsiloxane Surface," *Langmuir* 23(6):3118-3122 (2007), each of which is hereby incorporated by reference in its entirety). The composition of SU-8 can also be modified before its structuring to become hydrophilic after polymerization (Chen and Lee, "A Bonding Technique using Hydrophilic SU-8," *J Micromechanics Microengineering* 17:1978-1984 (2007), which is hereby incorporated by reference in its entirety). Fouling of the channel surface via nonspecific binding is an obvious concern for any microfluidic application. Anecdotal evidence suggests that SU-8 is less prone to this, but it is important to note that chemical treatment methods are also available for improving the performance of PDMS (Lee and Vörös, "An Aqueous-based Surface Modification of poly(dimethylsiloxane) with poly (ethylene glycol) to Prevent Biofouling," *Langmuir* 21:11957-11962 (2004), which is hereby incorporated by reference in its entirety).

Figure 4A:
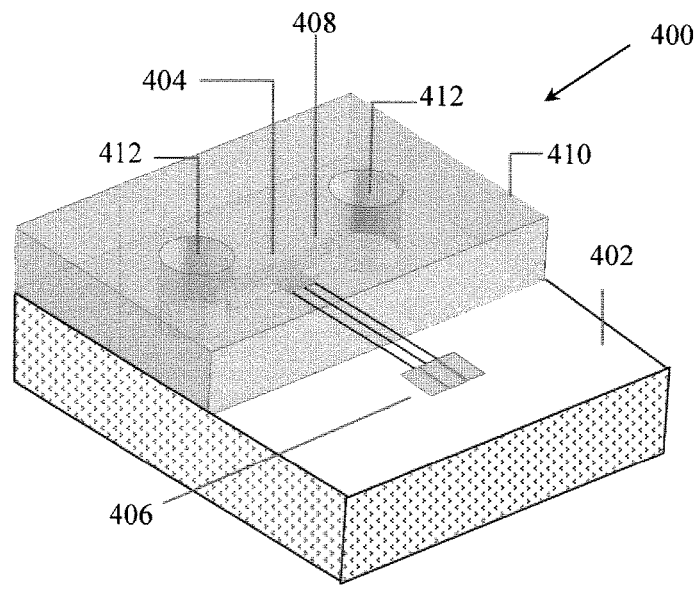
FIG. 4A is a perspective view illustrating one embodiment of a microfluidic device containing an electrochemical cell integrated into a flow channel of the microfluidic device.

FIG. 4A illustrates a PDMS-based microfluidic sensor 400. The bottom of the channel is a microfabricated chip 402 with a planar electrochemical cell 404 patterned on its surface. The electrodes formed on the surface of the chip are connected to bonding pads 406, and the electrodes are coated with a film of the present invention. A microchannel 408 is defined by the chip surface 402 and a PDMS slab 410 that is adhered to the surface of the chip using standard procedures. A sample port 412 and a reservoir port 414 are also defined by the PDMS slab, allowing for the sample to flow over the surface of the electrochemical cell. The sample transport is provided by, e.g., passive pumping (see Chen et al., "Computation of Transient Flow Rates in Passive Pumping Micro-fluidic Systems," *Lab. Chip.* 9:107-114 (2009); Chen et al., "Lab-on-Chip Flow Injection Analysis System without an External Pump and Valves and Integrated with an In Line Electrochemical Detector," *Anal. Chem.* 81:9955-9960 (2009), each of which is hereby incorporated by reference in its entirety).

Figure 4B:
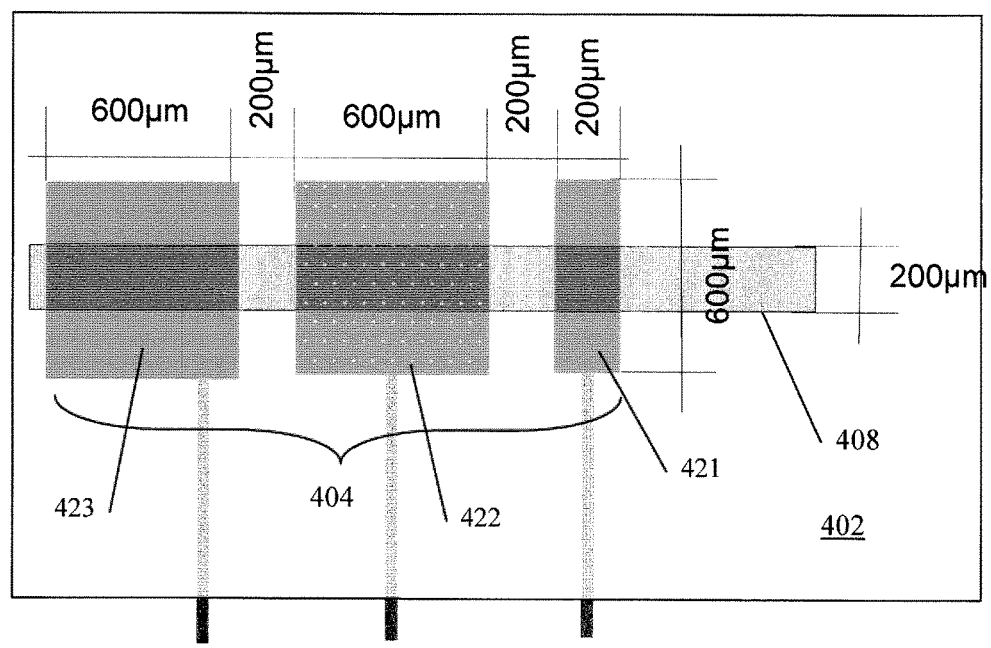
FIG. 4B illustrates the structure of a microdisc array comprising working, counter, and reference electrodes, with the working electrode covered by a coating of the present invention, and the microfluidic channel passing across each electrode of the array.

FIG. 4B illustrates the structure of the planar electrochemical cell 404 formed in the microfluidic sensor 400. The electrochemical cell 404 includes a microdisc array working electrode 422, counter electrode 423, and reference electrode 421. The working electrode 422 is covered with a coating of the present invention, and the microfluidic channel 408 is formed across all three electrodes of the array. As an alternative to a microdisc array, a microarray band or interdigitated array can be used.

As noted above, the electrochemical sensor or sensor array is intended to be in contact with a fluid sample. As such, during use, the electrochemical sensor is intended to be exposed to a fluid sample. To facilitate exposure to the fluid sample, a fluid sample can be drawn from the patient and then exposed ex vivo to the sensor or sensor array. The sensor or sensor array according to any embodiment described herein is suitable for ex vivo detection of bioavailable drug concentration.

Figure 5:
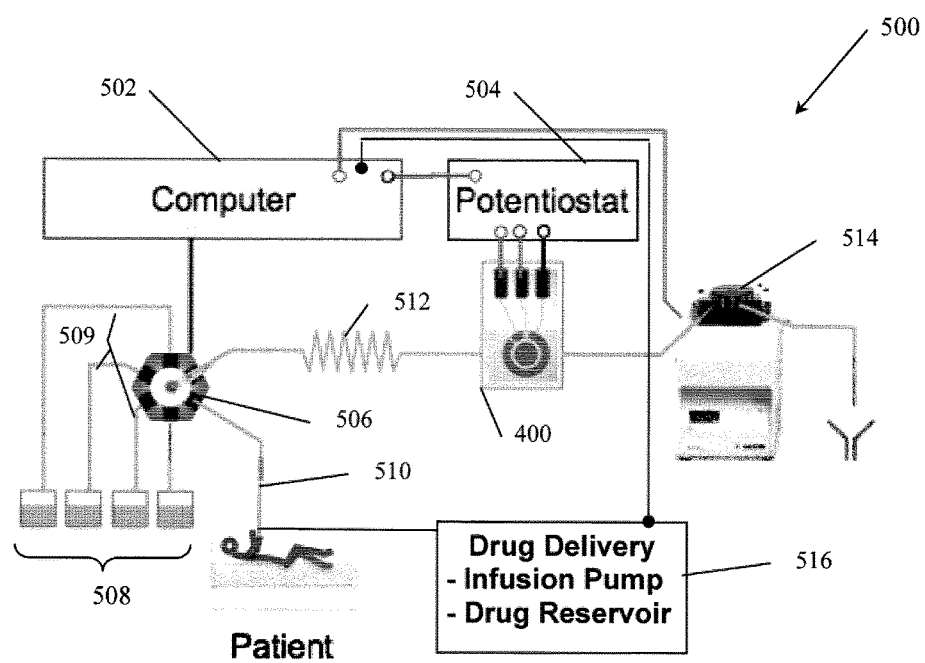
FIG. 5 illustrates one example of an ex vivo sensor device, which can be used for the feedback controlled delivery of propofol or other electrochemically active drugs or metabolites.

FIG. 5 illustrates one example of an ex vivo sensor device 500. Any computer or microprocessor controlled analyzer equipped with a flow-through electrochemical cell that incorporates the membrane coated electrochemical sensor can be used for the feedback controlled delivery of propofol or other electrochemically active drugs. In FIG. 5, a computer or microprocessor 502 controls a sampling valve 506 and peristaltic pump 514 for sampling blood from a patient via lines 510, 512 and for sampling standards and carrier solution (collectively, 508) via lines 509, 512. A potentiostat 504 is also controlled by computer/microprocessor 502 for the electrochemical measurements of the electrochemically active drug in blood samples and in the calibration standards using the microfluidic sensor 400. Depending on the measured concentration of the electrochemically active drug in the blood sample, a drug delivery device 516 under control of the computer/microprocessor 502 adjusts dosing of the electrochemically active drug to the patient based on the measurements. Although the microfluidic sensor as shown includes a three-electrode microarray, as described above, it should be appreciated that the electrochemical cell can contain any desired number of electrodes depending on the type of measurement operation performed.

Alternatively, during use, the sensor or sensor array may reside in a device that is retained in fluid communication with the fluid sample in vivo. Examples of this type of sensor construction include, without limitation, indwelling solid fibers with electrochemical sensor(s), collinear catheters (that is, a cylinder or fiber inside another) equipped with electrochemical sensor(s), and catheters having different proximal and distal sensors.

Figure 6:
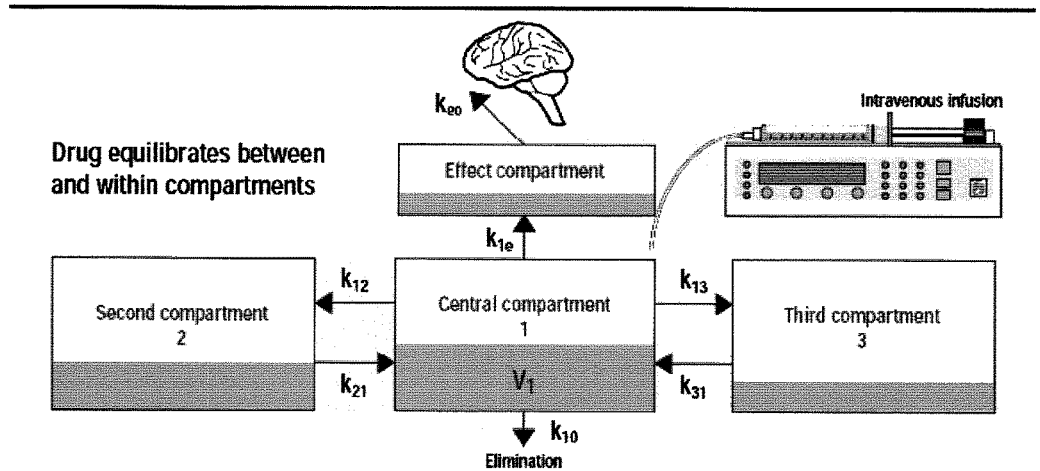
FIG. 6 illustrates that the bioavailable drug concentration can be detected in blood/lymph (central compartment), CSF (second compartment), or exhaled breath (third compartment).

The electrochemical sensor or sensor array of the present invention is particularly useful in combination with a target-controlled infusion drug delivery device. The design and construction of such drug delivery devices are well known in the art. The present invention involves modifying these known devices to include an electrochemical sensor or sensor array of the invention as a component in a feedback mechanism that is designed to control drug delivery (to the patient) based, at least in part, on the bioavailable drug concentration in a fluid sample from the patient (FIG. 6). Thus, rather than relying solely on pharmacodynamic models or physiological feedback mechanisms, the drug delivery device of the present invention also relies on the bioavailable drug concentration from the patient. As shown in FIG. 6, the bioavailable drug concentration can be detected in blood/lymph (central compartment), CSF (first compartment), or exhaled breath (third compartment).

Exemplary drug delivery devices that can be modified include those described in U.S. Pat. No. 7,220,240 to Struys et al., U.S. Patent Publ. Nos. 2007/0118075 to Kimmo et al. and 2006/0167722 to Struys et al., J. Glen et al., "The Development of 'Diprifusor': A TCI System for Propofol," *Anesthesia,* 53, Supplement 1, pp. 13-21 (1998); J. Gray et al., "Development of the Tehcnology for 'Diprifusor' TCI Systems," *Anesthesia*, 53, Suppl. 1, pp. 22-27 (1998), each of which is hereby incorporated by reference in its entirety.

Figure 7:
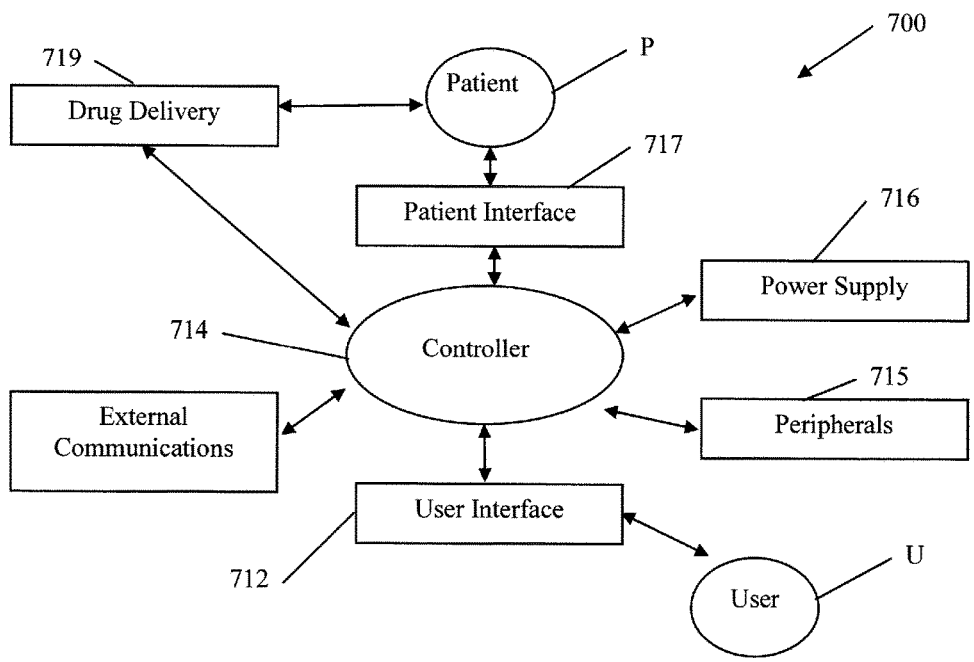
FIG. 7 illustrates a block diagram depicting one embodiment of a drug delivery system that is equipped with an electrochemical sensor of the invention.

With reference to FIG. 7, a block diagram depicting one embodiment of a drug delivery system 700 that is equipped with an electrochemical sensor of the invention is illustrated. The system 700 includes user interface 712, software controlled controller 714, peripherals 715, power supply 716, external communications 710, patient interface 717, and drug delivery 719, where sedation and analgesia system 700 is operated by user U to provide drug delivery (e.g., sedation and/or analgesia) to patient P. The basic structure of this sedation and analgesia system 700 is disclosed by U.S. Pat. No. 6,745,764 to Hickle, which is hereby incorporated by reference in its entirety; but the system is modified such that the patient interface 717 includes an electrochemical sensor of the present invention.

Briefly, the drug delivery 719 includes a drug reservoir (which preferably, during use, includes an electrochemically active drug of the type described above), and a pump in communication with the drug reservoir.

The patient interface 717 includes an electrochemical sensor of the present invention, which produces an electrochemical signal in the presence of the bioavailable drug. As noted above, the electrochemical sensor can be located ex vivo or in vivo. Regardless of its position with respect to the patient, the electrochemical signal produced is in direct correlation to an amount of bioavailable drug detected during a measuring event (i.e., within a patient fluid or vapor sample). The output of the electrochemical sensor is coupled to a detector which can be configured to convert the detected signal output from electrochemical sensor into a corresponding calibrated value. The detector can measure the electrochemical signal, e.g., the current, voltage, potential, impendence, conductance, or charge.

Using the sensor or sensor array of the present invention in combination with fluid samples containing known concentrations of a bioavailable form of a drug, it is possible to generate empirical data that correlates the detected electrochemical signal levels with the bioavailable or total drug concentration. The correlation function can be stored in the computer memory and used to calculate the bioavailable or total drug concentration from the measured data.

The controller 714 can include an input/output (I/O) card coupled through a data bus into a processor. The conditioned signal at the output of the detector is provided to an analog to digital converter (ADC) inside controller 714. The ADC converts the analog output of the detector to a corresponding digital value for processing by controller 714. The digital value of the detected electrochemical signal is provided to central processing unit (CPU)/processor via an internal bus. By way of example only, the ADC can be an 8-bit ADC, although other types of ADCs may also be used as known to those skilled in the art.

CPU/processor receives and processes the digital electrochemical signal from ADC. CPU/processor can be in the form of a single board computer which includes one or more microprocessors or CPUs. Controller 714 may be conveniently implemented using one or more general purpose computer systems, microprocessors, digital signal processors, and micro-controllers, programmed according to the teachings described and illustrated herein. For example, CPU/processor can be an Intel Core Duo® processor provided by Intel Corporation of Santa Clara, Calif. Alternatively, CPU/processor may be a special purpose processor designed and fabricated to carry out various aspects of this invention. For example, CPU/processor may be an application specific integrated circuit (ASIC) chip.

Figure 8:
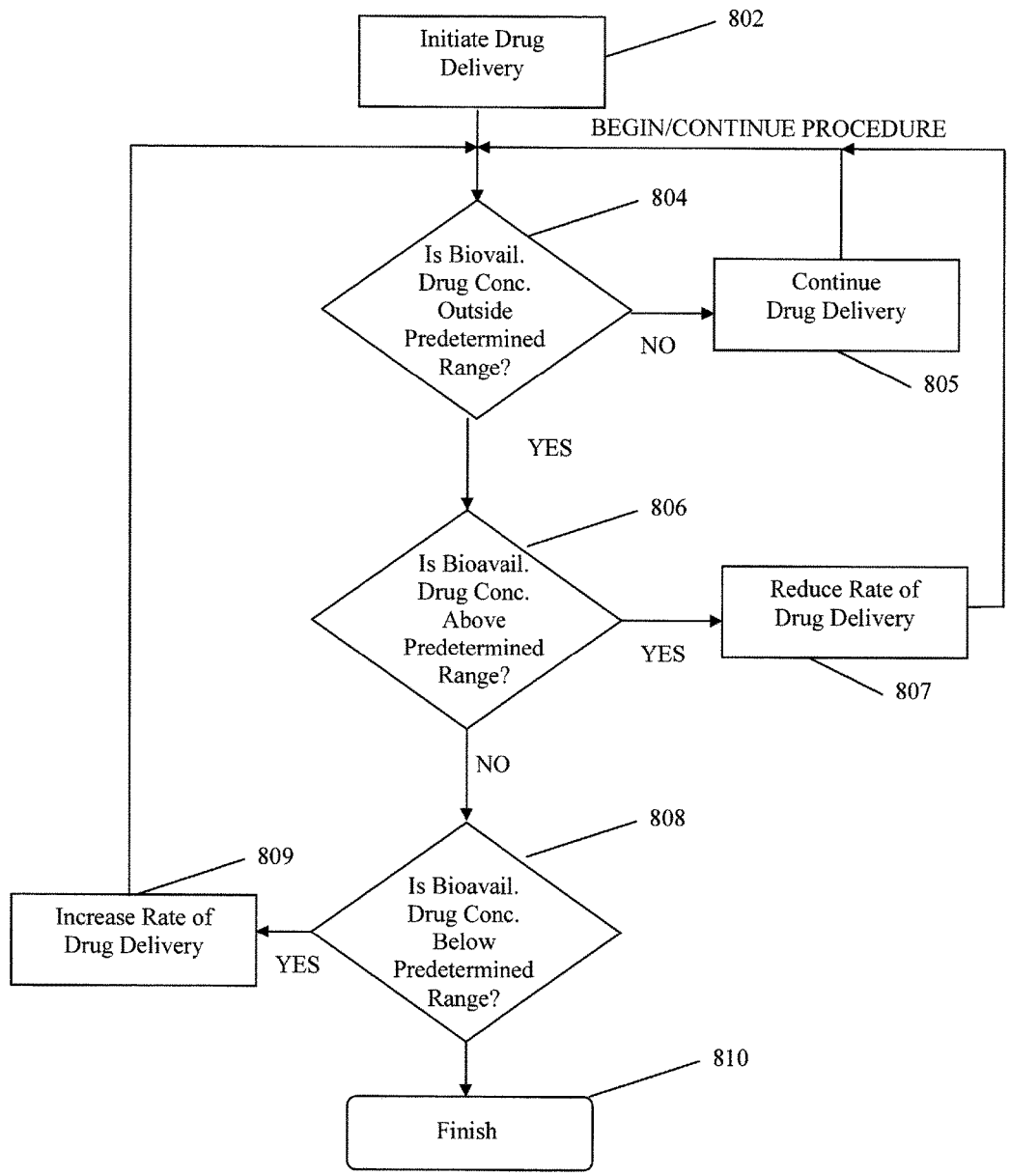
FIG. 8 is a diagram illustrating one method of modulating drug delivery.

CPU/processor is coupled to a memory that stores various settings for the delivery system 700. For example, memory stores one or more threshold values of the output electrochemical signal from electrochemical sensor, which threshold values represent the target range for the bioavailable drug concentration, i.e., minimum and maximum bioavailable drug concentrations. The memory can be a random access memory (RAM) and/or read only memory (ROM), along with other conventional integrated circuits used on a single board computer as are well known to those of ordinary skill in the art. Alternatively or in addition, the memory may include a floppy disk, a hard disk, CD ROM, or other computer readable medium which is read from and/or written to by a magnetic, optical, or other reading and/or writing system that is coupled to one or more processors. The memory can include instructions written in a computer programming language or software package for carrying out one or more aspects of the present invention as described and illustrated herein, although some or all of the programmed instructions could be stored and/or executed elsewhere. For example, instructions for executing steps outlined in FIG. 8 can be stored in a distributed storage environment where memory is shared between one or more controllers similar to controller 714.

Controller 714 can include an input/output (I/O) device (e.g., an I/O card) coupled to CPU/processor. The user interface 714 (e.g., display with keypad), external communications 710, peripherals 715, patient interface 717, and drug delivery 719 can be coupled to the controller 714 via and internal bus. The I/O device includes a bi-directional port for communication to/from other computing and/or electronic devices via a link. The port can also be used for charging the device via power supply 716, which can be a battery. By way of example only, the port can be a Universal Synchronous Bus (USB) port, although other types of communication and input/output ports may also be used, as known to those skilled in the art.

The internal bus is designed to carry data, power and ground signals, as known to one skilled in the art. By way of example only, internal bus can be a Peripheral Component Interconnect (PCI) bus, although other types of local buses (e.g., Small Computer System Interface or "SCSI") may also be used, as known to those skilled in the art.

User interface 712 can be a suitable display panel on which instructions and data are presented to a user in both textual and graphic format. In addition, display 712 can include a touch screen also coupled to the I/O device for accepting input from a user (e.g., a medical professional). The display can display the concentration of the bioavailable drug concentration based on the output electrochemical signal that is generated by the electrochemical sensor. Further, the display can be substituted by or used in conjunction with an audio device (e.g., a speaker, a buzzer, or a beeper alarm) controlled by CPU/processor to indicate whether the bioavailable drug concentration is too high or too low.

The controller 714 receives power from a power supply 716. Power supply 716 can be a battery or a direct pluggable outlet to a main power-line. Alternatively, power supply 716 may be a switched mode power supply (SMPS) commonly used in computer systems, although other forms for powering controller 714 using power supply may also be used, as known to those skilled in the art.

The controller 714 preferably carries out a PID controller algorithm using the input from the electrochemical sensor. The PID controller involves three separate parameters: the Proportional, the Integral and Derivative values. The Proportional value determines the reaction to the sensed bioavailable drug concentration, the Integral value determines the reaction based on the average bioavailable drug concentration, and the Derivative value determines the reaction to the rate at which the bioavailable drug concentration has been changing. In the context of the present invention, any one of these parameters or the weighted sum of any two (or all three) of these parameters can be used to adjust the rate of drug discharge by the drug delivery 719.

From the foregoing, it should be appreciated that the present invention also relates to a method for electrochemical detection of bioavailable drug concentration in a fluid sample, which includes the steps of: exposing a fluid sample to an electrochemical sensor comprising one or more electrodes and a coating that surrounds the one or more electrodes, which coating is capable of partitioning the bioavailable drug directly from the fluid sample; and detecting an electrochemical signal in the coating that relates to a concentration of bioavailable drug in the fluid sample.

This system and method can also be utilized in detecting the concentration of bioavailable drug in a vapor sample such as exhaled breath. In this embodiment, the sensor is positioned within the exhalation side of a ventilation/respiratory circuit.

The present invention also relates to a method of modulating drug delivery that includes the steps of: exposing a fluid or vapor sample obtained from a patient to an electrochemical sensor of the present invention, the electrochemical sensor capable of detecting an electrochemical signal in the coating that relates to a concentration of bioavailable drug in the fluid or vapor sample, and then modulating delivery of the drug into a patient based on the concentration of the bioavailable drug in the fluid or vapor sample.

Because the patient receiving the drug is monitored continuously during the procedure for which the drug is being administered, the detection of bioavailable drug concentration is preferably performed repeatedly (periodically or episodically) during a surgical procedure such that appropriate feedback control is provided to maintain the bioavailable drug concentration within an optimal range. While the frequency of the detection step can vary depending on the pharmacokinetics of a particular drug, it is generally desirable to repeat the detection procedure at least every 5 minutes, more preferably at least every 2 to 3 minutes. More frequent detection procedures can also be carried out.

As a consequence of the frequent monitoring of bioavailable drug concentration, the output from the electrochemical sensor can be used to modify operation of the drug pump in real time (as noted above). Preferably, adjustments in drug delivery, if any, are made instantaneously following the detection event (i.e., within the capacity of the processor control system). The method of modulating drug delivery can include the embodiment illustrated in FIG. 8.

Upon initiation of drug delivery at step 802, either via bolus or predetermined delivery rate, drug delivery begins. This step may occur at a predetermined time prior to surgery. Prior to beginning the surgical procedure and periodically during the course of the surgical procedure, the query at step 804 initiates measurement of the bioavailable drug concentration using the electrochemical sensor of the present invention. If the bioavailable drug concentration remains with the predetermined range (e.g., about 3 to about 8 µg/ml for Propofol as an anesthetic, or about 1 to about 2 µg/ml for Propofol as a sedative), then at step 806 the existing drug delivery rate is maintained. (If this is the first measurement with the bioavailable drug concentration within the target range, the surgical procedure can begin at this time.) If the bioavailable drug concentration is outside the predetermined range, then the output of the electrochemical sensor is assessed at steps 806 and 808, respectively, to determine whether the detected bioavailable drug concentration is above or below the predetermined range. If the bioavailable drug concentration detected during a single detection step is above an acceptable range, then the rate of drug delivery can be reduced or entirely withdrawn for a short duration at step 807. A reduction can be automated via the PID controller. If the bioavailable drug concentration detected during a single detection step falls below an acceptable range, then an immediate change in the rate of drug delivery can be made, a single bolus can be administered, or both, at step 809. An increase can be automated via the PID controller. These steps can be carried out using a suitable software algorithm, and they can be repeated at periodic or episodic intervals during the surgical procedure. Upon completion of the surgical procedure, the drug delivery protocol can be withdrawn at step 810.

As is known in the art, the software algorithm (PID controller) used to adjust drug delivery rate can also rely on one or more patient physiological response parameters, including blood pressure, heart rate, temperature, and EEG parameters. See Wang et al., "New Target Controlled Infusion Using a Hybrid Physiology Based Pharmacokinetic Model," *IEEE* 1822-1824 (2008) (ISBN: 978-1-4244-1747-6), which is hereby incorporated by reference in its entirety. In addition to the foregoing, it should be appreciated by persons of skill in the art that drug administration is not limited to surgical procedures, but can also be effectively used in other settings, e.g., during intensive care or post-operative care.

EXAMPLES

The following examples are provided to illustrate embodiments of the present invention but are by no means intended to limit its scope.

Materials and Methods for Examples 1-3

Materials:

2,6-Diisopropylphenol (propofol) was purchased from Sigma Aldrich (St. Louis, Mo.) and prepared first as a 10 mM stock solution in 0.1 M NaOH, before diluting to a 1 mM secondary stock solution in phosphate buffer (PBS) for use in the experiments. The PBS buffer (pH ~7.2) was prepared as a mixture of 0.1 M $KH_2PO_4$, 0.1 M KCl and 0.045 M NaOH. All other reagents used in this study were purchased commercially from Sigma Aldrich and were of ACS grade unless stated otherwise. The aqueous solutions were prepared with water purified by a Milli-Q Gradient A10 System (Millipore Corp., Billerica, Mass.).

Membrane Solutions:

PVC membrane solutions were generally prepared as 250 mg quantities, consisting of ~25 wt. % PVC, ~50 wt. % plasticizer, ~22 wt. % organic electrolyte and ~3 wt. % ion-exchange salt. This mixture was then dissolved in 2.5 mL tetrahydrofuran (THF). The PVC (high molecular weight), and its plasticizers: 2-nitrophenyl octyl ether (o-NPOE), bis(2-ethylhexyl) sebacate (DOS) and 1-octanol were selectophore grade. The organic electrolyte, tetradodecylammonium tetrakis(pentafluorophenyl) borate (TDDATPFPhB) was prepared by metathesis reaction between tetradodecylammonium chloride (TDDACl) and potassium tetrakis(pentafluorophenyl) borate (KTPFPhB) (Boulder Scientific Company, CO) in dichloromethane, followed by a liquid phase extraction of the product using de-ionized (DI) water. The organic electrolyte, bis(triphenylphosphoranilidine)ammonium tetrakis[3,5,bis(trifluoromethyl)phenyl]borate (BTPPATFPhB) was prepared the same way from bis(triphenylphosphoranylidene) ammonium chloride (BTPPACl) (Sigma Aldrich) and sodium tetrakis[3,5bis(trifluoromethyl)phenyl]borate dihydrate (NaTFPhB) (Dojindo Laboratories Gaithersburg, Md., USA). KTPFPhB also served as the ion-exchange salt, or NaTFPhB was used. The specific compositions of each PVC membrane solution mixture used during the course of this work are described in Table 1. The membrane solutions differ from each other primarily in terms of the plasticizer, the organic electrolyte, or the ion-exchange salt content.

TABLE 1

Composition of PVC Membrane Solutions (wt %) for Spin Coating the GC Electrode Surface. ~250 mg quantities were dissolved in 2.5 mL THF

| PVC Membrane Solutions | | I | II | III | IV | V |
|---|---|---|---|---|---|---|
| Polymer | PVC | 25.5 | 25.1 | 25.5 | 25.0 | 25.5 |
| Plasticizer | o-NPOE | 50.9 | | | | |
| | DOS | | 49.9 | 49.6 | 49.8 | |
| | 1-octanol | | | | | 49.5 |
| Electrolyte | TDDATPFPhB | 21.2 | 22.6 | 21.9 | | 21.8 |
| | BTPPATFPhB | | | | 21.8 | |
| Ion-exchange Salt | NaTFPhB | 2.4 | | 3 | 3.4 | 3.2 |
| | KTPFPhB | | 2.4 | | | |
| Solvent | THF | (a) | (b) | (c) | (c) | (c) |

†ACS grade THF generally contains butylated hydroxytoluene (BHT) as antioxidant. BHT is an electrochemically active compound with very similar structure to propofol. To avoid possible interference from BHT, the THF used to dissolve the membrane solution ingredients was either cleaned by column chromatography(a), or distilled before use(b), or an inhibitor-free(c) THF was used.

Electrodes and Methods:

Cyclic voltammetry (CV) and chronoamperometry (CA) experiments were performed in a 3-electrode cell, using a CH Instruments Model 900 potentiostat (CH Instruments Inc., TX). In these measurements Ag|AgCl|3.0 M KCl (CH Instruments) and a platinum wire served as the reference and counter electrode, respectively. The potential of the reference electrode was regularly checked versus a saturated calomel reference electrode. Readings for the Ag/AgCl reference electrode were generally recorded as −35.3/mV in 3.0 M KCl. For details on the theory and application of CV and CA methods the book of Bard and Falkner is recommended (Bard et al., *Electrochemical Methods*. 2nd ed.; John Wiley & Sons, Inc.: New York (2001), which is hereby incorporated by reference in its entirety.

For the working electrode, a PVC membrane coated glassy carbon (GC) (Ø=3 mm) was used (BASi, IN). The working electrode was first polished (0.3 µm and 0.05 µm alumina slurry), then rinsed and sonicated in DI water, and dried. The electrode was spin-coated with a PVC membrane using a drill press. The electrode was dipped into a PVC membrane solution and rotated for 20 seconds at 1100 rpm and left in an up-right position until the complete evaporation of THF (~1 hour). This protocol resulted in a few µm thick PVC membrane coating on the electrode surface. Prior to electrochemical experiments, the PVC membrane-coated electrodes were soaked in PBS for 15 minutes.

Electrochemically oxidizable impurities in the membrane may interfere with the voltammetric determination of the analyte. In the accompanying Examples, impurities in KTPFPhB resulted in an oxidation peak at ~1.6 V in the cyclic voltammograms recorded in the background electrolyte. This interference was minimized by implementing an electrochemical pre-treatment protocol in which the potential of the membrane coated electrode was cycled between 0.8 and 1.8 V for 100 scans at 0.1 Vs$^{-1}$ in the background electrolyte prior to exposing the membrane coated sensor to any solution containing propofol, the target analyte. The electrochemical pre-treatment step was no longer required once a high purity KTPFPhB was used for the membrane solutions.

Example 1—Cyclic Voltammetry with the PVC Membrane Coated GC Electrode

In this Example, a plasticized PVC membrane coated GC electrode was used for the measurement of propofol in the presence of interfering compounds at physiologically relevant pH values. As plasticizers, o-NPOE and DOS were used with dielectric constants of 23.9 and 3.9, respectively (Mohr, OPTICAL CHEMICAL SENSORS 297-321, Baldini et al., eds., Springer (2006), which is hereby incorporated by reference in its entirety). Based on previous CV experiments with propofol in acetonitrile, no or minimal electrode fouling was expected when the electrochemical oxidation of propofol is performed in an organic phase.

To perform voltammetric measurements with the plasticized PVC membrane coated electrode, the membranes were prepared with an organic electrolyte (TDDATPFPhB) in combination with an ion-exchange salt (e.g., KTPFPhB), which served as the background electrolyte. Based on the early works of Nieman (Nieman et al., *Analytica Chimica Acta* 170:359-363 (1985), which is hereby incorporated by reference in its entirety) and Amman (Ammann et al., *Analytica Chimica Acta* 171:119-129 (1985), which is hereby incorporated by reference in its entirety), these and similar additives are commonly used to reduce the resistance of liquid membrane ion-selective electrodes. The organic electrolyte has been used in combination with an ion-exchange salt because it provided the lowest resistance (Ammann et al., *Analytica Chimica Acta* 171:119-129 (1985), which is hereby incorporated by reference in its entirety). In general, the primary role of the ion-exchange salt in ion-selective membranes is to improve the permselectivity of the membrane. The permselectivity of the PVC membrane coating during the voltammetric determination of propofol improves the selectivity of the sensor against negatively charged interfering compounds like ascorbate anion. However, in this work the ion exchange salt was incorporated into the membrane with an additional consideration. It was assumed that the oxidation of propofol generates positively charged cationic species, e.g., phenoxonium ions (Morrow, in ORGANIC ELECTROCHEMISTRY, ed. Lund et al., Marcel Dekker, Inc.: New York, Basel (2001), which is hereby incorporated by reference in its entirety) in the membrane, and the excess positive charge is compensated for by the release of hydrophilic cations from the ion exchange salt into the solution.

Figure 9:
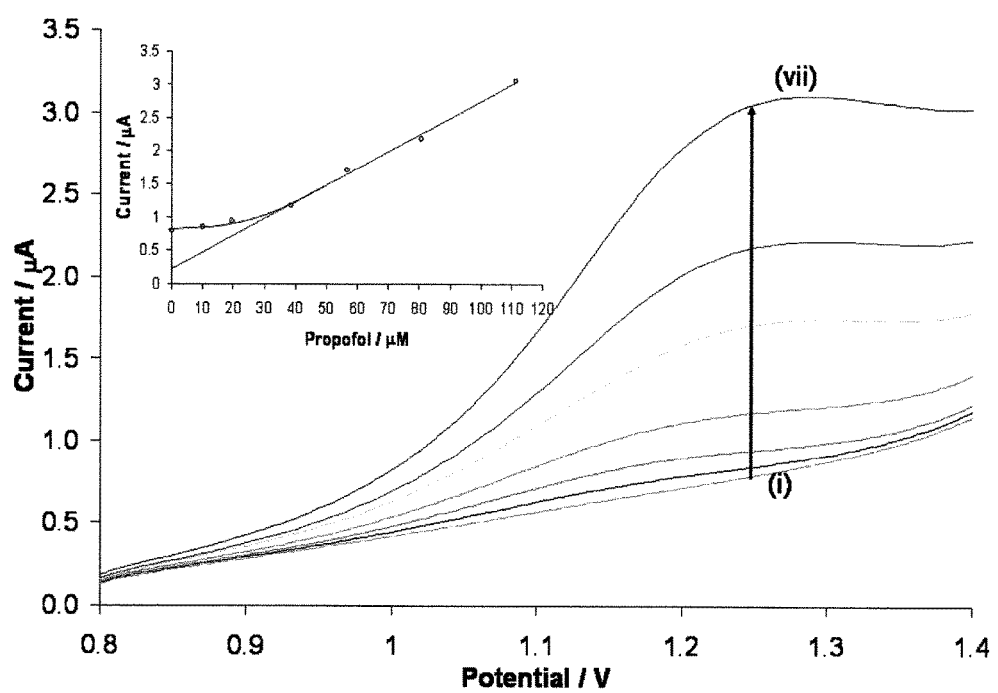
FIG. 9 shows forward CV scans recorded with a PVC-membrane coated GC electrode (Solution I), for (i)=0 µM; (ii)=9.9 µM; (iii)=19.6 µM; (iv)=38.5 µM; (v)=56.6 µM; (vi)=80.5 µM; (vii)=111.1 µM propofol in PBS. Inset: Calibration curve for propofol based on peak current measurements at 1.25 V.

Cyclic voltammetry (CV) experiments performed with the PVC membrane coated electrode in PBS buffer containing different concentrations of propofol showed a concentration dependent oxidation peak at ~1.25 V. The traces of the forward scans recorded at 0.1 Vs$^{-1}$, and the calibration curve constructed from the peak current values are shown in FIG. 9. Using the residual mean standard deviation (RMSD)

and slope value (S) of the calibration curve between 40 and 111.1 M, a detection limit (DL) of 8.8 µM was calculated (DL=3×RMSD/S). By considering the reproducibility of the background current (the standard deviation of the background current recorded in three CV scans for the PBS background solution) an improved DL of 2.2 µM (DL=3× STDV/S) was calculated.

CVs recorded with the PVC membrane coated electrode in PBS containing 111.1 µM propofol were very similar to the CVs recorded in acetonitrile. No electrode passivation or decrease in the peak current was detected for a series of continuous scans (6 in total). The peak current increased linearly with propofol concentration. The traces of the forward scans recorded at 0.1 Vs$^{-1}$, and the calibration curve constructed from the peak current values at 1.25 V are shown in FIG. 9.

Example 2—Chronoamperometry with the PVC Membrane Coated GC Electrode

Figure 10:
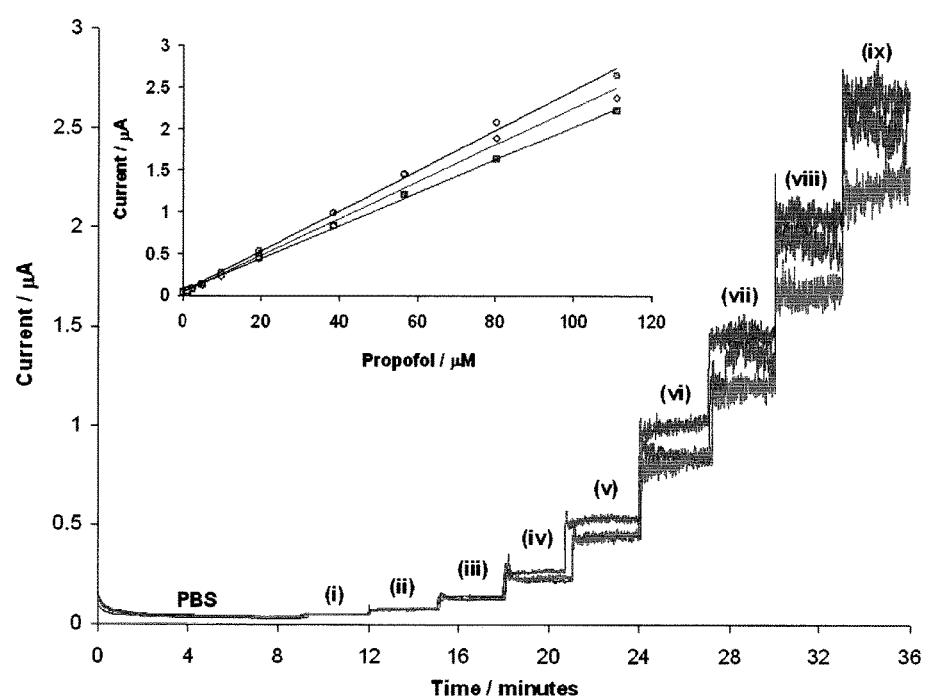
FIG. 10 shows CA response of PVC-membrane coated GC electrode (Solution I), for (i)=1.25 µM; (ii)=2.5 µM; (iii)=4.98 µM; (iv)=9.9 µM; (v)=19.6 µM; (vi)=38.4 µM; (vii)=56.6 µM; (viii)=80.5 µM; (ix) 111.1 µM propofol in PBS buffer. Top inset: Calibration curves for propofol based on current measurements after 2 minutes of each addition.

For continuous monitoring, chronoamperometry (CA) is a better alternative than CV. In CA experiments the charging current is smaller and the detection limit (DL) is lower. The CA response of three freshly prepared PVC membrane coated sensors for propofol in PBS is shown in FIG. 10 (Table I, solution I). Based on the CV experiments shown in FIG. 9, a potential of 1.2 V was applied vs. Ag|AgCl|3.0 M KCl reference electrode. Propofol concentration of the solution was increased by injecting aliquots of propofol standards at 3 minute intervals into a continuously stirred PBS background solution. As can be seen from FIG. 10, the response of the PVC membrane coated electrode is fast, and the sensor-to-sensor reproducibility is very good. The differences in the slopes of the calibration curves are related to the differences in the thickness of the organic membrane coatings on the GC electrode. Propofol sensors with thicker membrane coatings have reduced sensitivity and slower response compared to sensors with thinner membranes.

Due to concerns about performing voltammetric measurements in a resistive organic film, o-NPOE, which has a relatively large dielectric constant ($\epsilon_r$=23.9) (Mohr, OPTICAL CHEMICAL SENSORS, pp. 297-321, Baldini et al., eds., Springer (2006), which is hereby incorporated by reference in its entirety), was initially used as the plasticizer in the PVC membrane coatings (FIG. 10). However, once it was realized that the resistance of the membrane, due to its small thickness and large organic salt content was not critical, other plasticizers were evaluated. The different membrane coatings resulted in CVs with significantly different peak potentials and peak currents. CA experiments with the DOS plasticized membrane coated GC electrodes were performed with the same protocol as before, but with a different applied potential value.

To study the response of the membrane coated propofol sensor in the presence of easily oxidizable compounds that may interfere with the determination of propofol in whole blood, serum, or plasma, similar triplicate measurements were performed in the presence of 3 mM ascorbic acid (AA) and 1 mM 4-acetamidophenol (APAP). The selected concentrations of AA, APAP, and BSA are at the high end of physiologically relevant concentrations. In these experiments the samples contained also 5% bovine serum albumin (BSA). The influence of albumin on the response of the propofol sensor was tested because albumin is the most abundant plasma protein which may influence the response of an electrochemical sensor when adsorbed to the surface. In addition, it is known that up to 96% of propofol is bound to albumin (Bhattacharya et al., J. Biol. Chem. 275:38731-38738 (2000); Schywalsky et al., Arzneimittel-Forsch. 55:303-306 (2005), each of which is hereby incorporated by reference in its entirety), i.e., in the presence of albumin the free propofol concentration in the solution is significantly reduced compared to its nominal value.

Propofol detection in the presence of these particular interferents was first evaluated individually and then in a mixture of all three (in order to model measurements recorded in patient's serum or whole blood).

Example 3—Limit of Detection for Propofol with the Membrane-Coated Sensor

IUPAC defines the limit of detection as the smallest concentration (or quantity) that can be detected in an analytical procedure with a given certainty (Freiser et al., COMPENDUM OF ANALYTICAL NOMENCLATURE. DEFINITIVE RULES 1987, Blackwell Sci. Publ., Oxford, (1987), which is hereby incorporated by reference in its entirety). This concentration is derived from the mean of the measured signal in the blank ($\bar{x}_{bi}$), the standard deviations of the blank measurement ($s_{bi}$) and the slope of the analytical calibration curve (S) as $c_{DL}^1 = (x_L - \bar{x}_{bi})/S$, where $x_L = \bar{x}_{bi} + 3s_{bi}$.

The detection limit for propofol determination with the membrane coated sensor in cyclic voltammetric experiments (FIG. 9) by considering the standard deviation of the background current recorded in repeated CV scans (n=3) was calculated as $C_{DL}^1$=2.2 µM. In monitoring experiments, in addition to the smallest concentration that can be determined, the resolution of the concentration measurements is also very important. The resolution of the measurement is defined as the minimum difference between two concentrations that can be distinguished with a given probability. The resolution of the concentration measurements ($c_{DL}^2$) in this work has been calculated as $C_{DL}^2$=3×RMSD/S, where RMSD is the residual mean standard deviation of the data points of the calibration curve around the best line fit and S is the slope of the fitted line. By considering the peak current values recorded in the CV experiments between 40 and 111.1 µM (FIG. 9 inset) $C_{DL}^2$=8.8 µM was calculated. $c_{DL}^2$ is greater than $c_{DL}^1$ because the scatter of the data points around the best fit line is much larger at high concentrations than at low concentrations.

Figure 11A:
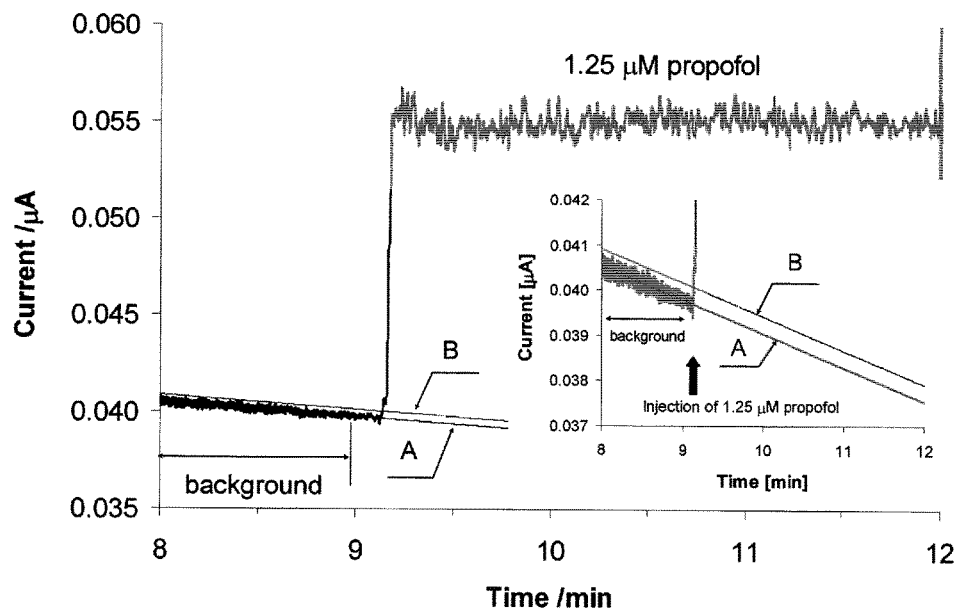
FIGS. 11A-B illustrate the CA response of a PVC-membrane coated GC electrode in PBS (11A) and in PBS containing 3 mM AA, 1 mM APAP and 5% BSA (11B). In both experiments the stirred background solution was spiked with 1.25 µM of propofol at ~9 minutes. In both of FIGS. 11A-B, (A) is a regression line fitted to data points measured in the background one minute before spiking the background with a propofol standard, and (B) a line with the same slope as line A but shifted parallel to line A by a value of 3 times of the RMSD of the points around line A. It represents a hypothetical average current following a concentration change corresponding to the theoretical detection limit. The inset in FIG. 11A shows a section of the background current on an expanded current scale with lines A and B.
Figure 11B:
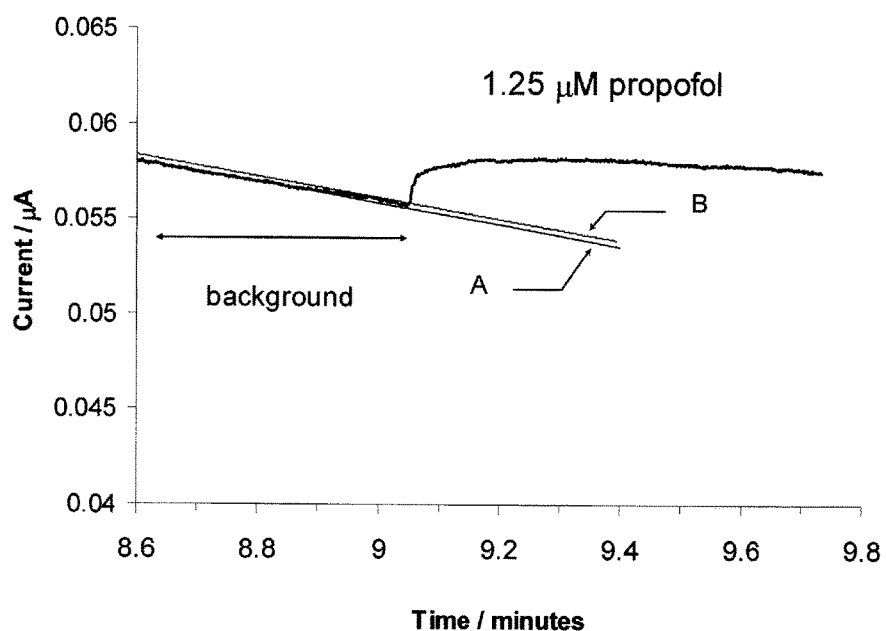

In FIGS. 11A-B, a close-up of the CA response for 1.25 µM propofol in PBS (11A) and in PBS containing 3 mM AA, 1 mM APAP and 5% BSA (11B) is shown in combination with details on the evaluation of $c_{DL}^1$ based on the background current noise. First a line was fitted to a one minute segment of the background current (just before the first addition of propofol) and the RMSD of the data points around the line was determined (RMSD$_{bgc}$) (Line A in the figures). Next, a second line was plotted parallel to line A in a distance of 3×RMSD$_{bgc}$ (Line B in the FIGS. 11A-B). This second line represents a theoretical current response in a solution with a concentration equal to the detection limit of the method. A comparison of the current change recorded upon the addition of 1.25 µM propofol and the current change equal to 3×RMSD$_{bgc}$ (the shift between line A and B in the inset of FIG. 11A) indicates impressive DL values. The detection limits and resolutions for propofol in chronoamperometric measurements using a GC working electrode with different membrane coatings in PBS, and in PBS containing a variety of potential interferences are summarized in Table 2. The resolutions of the CA measurements ($c_{DL}^2$) were calculated as above, using the slope and the RMSD data of the calibration curve ($c_{DL}^2$=3×RMSD/S). As shown in FIG. 11B, the interfering compounds increased the background current and decreased the slope of the calibration curves.

the bare GC electrode. This large decrease in the sensitivity for AA and APAP compared to an uncoated electrode is obtained because almost no AA or APAP is extracted into the

TABLE 2

Detection Limits ($c_{DL}{}^1$) and Resolutions ($c_{DL}{}^2$) for Propofol Measurements

| PLASTICIZER | MEMBRANE SOLUTION | BACKGROUND | LINEAR RANGE [μM] | $AVG_{c_{DL}{}^1}{}^\dagger$ [μM] | $AVG_{c_{DL}{}^2}{}^\dagger$ [μM] |
|---|---|---|---|---|---|
| o-NPOE | I | PBS | 0-56.6 | 0.03 ± 0.01 | 1.1 ± 0.2 |
|  | I | 3 mM AA* | 0-56.6 | 0.04 ± 0.05 | 2.0 ± 1.0 |
|  | I | 1 mM APAP* | 0-56.6 | 0.08 ± 0.02 | 4.6 ± 0.9 |
|  | I | 5% BSA* | 5.0-56.6 | 2.2 ± 3.1 | 14.5 ± 1.8 |
|  | I | MIXED‡ | 2.5-109.8 | 0.5 ± 0.4 | 28.2 ± 5.2 |
| DOS | II | PBS | 0-111.1 | 0.12 ± 0.05 | 4.3 ± 0.4 |
|  | II | MIXED‡ | 0-111.1 | 3.0 ± 0.3 | 4.5 ± 2.3 |
|  | III | PBS | 0-56.6 | 0.013 ± 0.004 | 5.5 ± 1.4 |
|  | III | MIXED‡ | 0-56.6 | 0.6 ± 0.4 | 4.3 ± 1.2 |
|  | IV | PBS | 0-56.6 | 0.022 ± 0.006 | 2.2 ± 0.6 |
|  | IV | MIXED‡ | 9.9-111 | 2.1 ± 1.7 | 12.6 ± 0.2 |

The membrane compositions are provided in Table I. The DL values are provided with their standard deviations (n = 3).
†$c_{DL}{}^1$ = 3 × $RMSD_{bgc}$/S; $c_{DL}{}^2$ = 3 × RMSD/S where $RMSD_{bgc}$ and RMSD were calculated by fitting a line to a section of the background current or the points of the calibration curve, respectively. The slope values (S) were calculated by least square regression in the concentration range quoted as linear range.
‡MIXED = 3.0 mM AA + 1.0 mM APAP + 5% w/v BSA, in PBS.
*PBS containing ascorbic acid (AA), or 4-acetamidophenol (APAP) or bovine serum albumin (BSA) as interferents.

In summary, the results in Table 2 show that propofol can be determined in PBS with the plasticized PVC membrane coated GC electrode down to nanomolar concentrations. Sub-micromolar detection limits could be achieved even in the presence of a large excess of easily oxidizable compounds, like AA and APAP. However, in the presence of physiologically relevant levels of albumin the detection limit is shifted towards somewhat larger concentrations. This shift in the DLs toward larger concentrations is a consequence of the decrease in the sensitivity of the measurements in the presence of albumin. The slope of the calibration curves were 6 to 18 times larger in PBS than in the MIXED background electrolyte (PBS with 3 mM AA, 1 mM APAP and 5% BSA) using the DOS or o-NPOE plasticized PVC membranes on the surface of the GC working electrode, respectively. Parallel to the decrease in the slope values in the MIXED background the RMSD values of the calibration points around the regression lines increased which made the calculated resolution of the measurements worse.

A comparison of the compiled values in Table 2 shows that the response range, detection limit ($c_{DL}{}^1$) and resolution ($c_{DL}{}^2$) values were better for the GC electrodes coated by DOS plasticized than o-NPOE plasticized membranes.

Figure 12A:
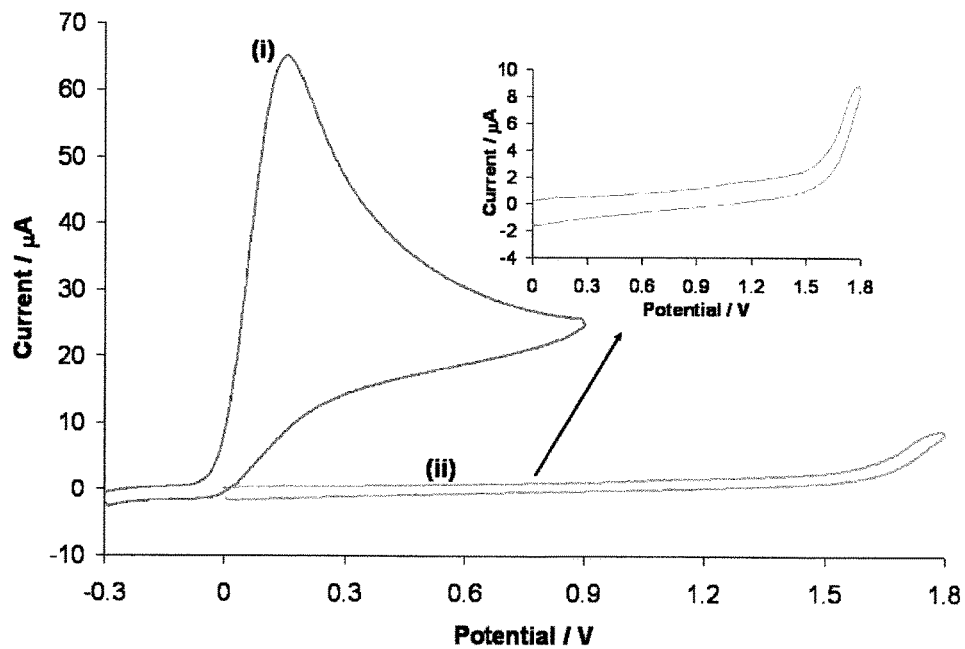
FIG. 12A shows CV scans recorded for 3.0 mM AA in PBS using a (i) bare GC electrode; and (ii) PVC-membrane coated GC electrode. Scan rate, $v=0.1$ $Vs^{-1}$.
Figure 12B:
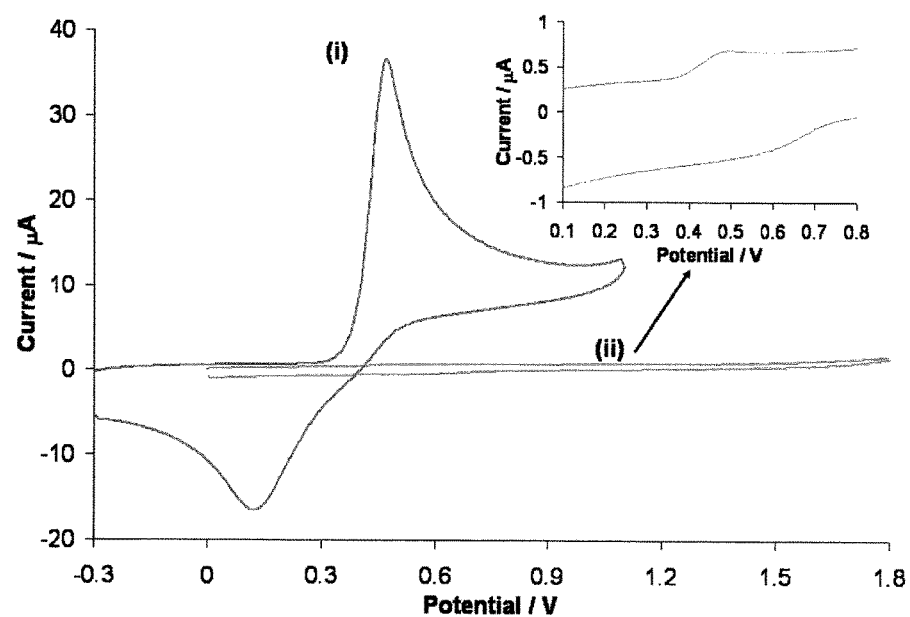
FIG. 12B shows CV scans recorded for 1.0 mM APAP in PBS using a (i) bare GC electrode; and (ii) PVC-membrane coated GC electrode. Scan rate, $v=0.1$ $Vs^{-1}$.
Figure 13:
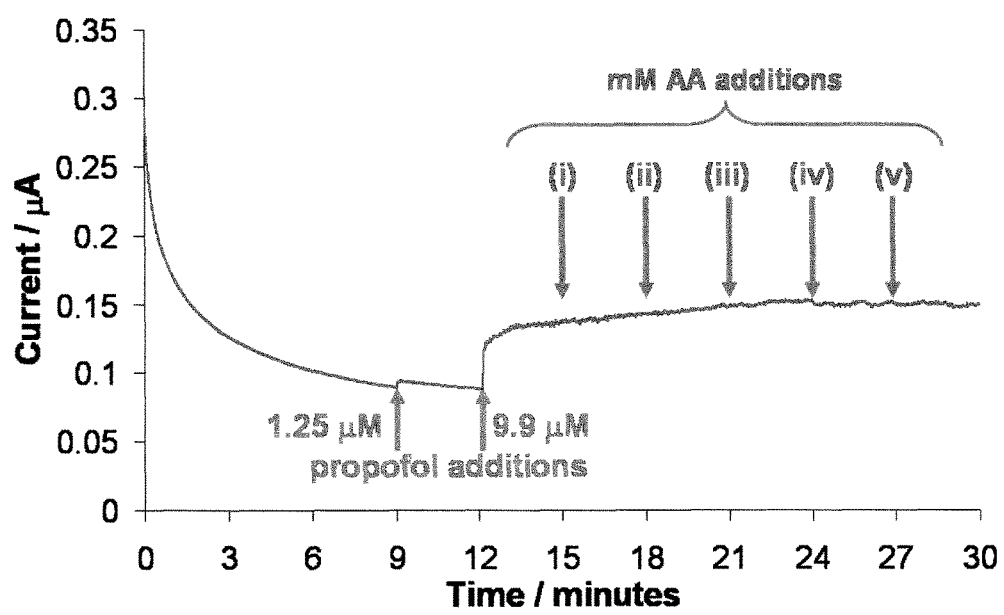
FIG. 13 shows the CA response recorded for 1.25 & 9.9 µM propofol in a PBS solution containing 5% w/v BSA, followed by additions of (i) 0.53 mM; (ii) 1.0 mM; (iii); 1.48 mM; (iv) 1.98 mM; (v) 3.08 mM AA at 3 minute intervals.

Example 4—Selectivity of the Propofol Sensor: Importance of the Partition Coefficients Between the Membrane and the Aqueous Solution To elucidate the impressive detection limit of the propofol sensor in the presence of the most common electrochemical interferences (Table 2), CV scans were recorded both with the bare GC electrode and PVC membrane-coated GC electrode in 3 mM AA and 1 mM APAP solutions. The results of these experiments are shown in FIG. 12A-B. The influence of the PVC membrane coating on the CV response is remarkable in both experiments. No measurable oxidation peak is obtained with the PVC membrane-coated electrode for 3 mM AA and the peak current related to the oxidation of APAP was about 140 times smaller with the PVC membrane-coated electrode in 1 mM APAP solution compared to the bare GC electrode. This large decrease in the sensitivity for AA and APAP compared to an uncoated electrode is obtained because almost no AA or APAP is extracted into the highly hydrophobic membrane, and because the diffusion coefficients are much smaller in the membrane compared to the aqueous solution. The anion exclusion properties of the membranes with KTPFPhB or NaTFPhB content, is an additional benefit with respect of anionic interferences like ascorbate anion. FIG. 13 shows that the chronoamperometric current in a sample with 10 μM propofol remains constant upon the stepwise change of AA concentration in that sample from zero up to 3 mM.

In the cyclic voltammetry experiments with the membrane coated electrode (FIG. 9) the peak currents increased linearly with the square root of the scan rate between 10 and 150 mV/s, and were barely influenced by the rotation rate between 400 and 1600 rpm indicating that the diffusion in the membrane dominates the mass transfer rate. Based on the scan rate dependence of the peak current for the membrane-coated sensor in propofol solutions, it was assumed that the Randles-Sevcik equation (Eq. 6.2.19 in Bard and Falkner, *Electrochemical Methods*, John Wiley and Sons, New York (2001), which is hereby incorporated by reference in its entirety) can be used to describe the peak current dependence on the concentration. With this assumption, the current ratio measured with the coated and uncoated sensor (Equation 1) can be used to calculate the partition coefficient $$\left(P_{mw} = \frac{c_m}{c_w}\right)$$

of an electrochemically active solute between the membrane and aqueous solution.

$$\frac{i_m}{i_w} = \frac{D_m^{1/2}}{D_w^{1/2}} \cdot \frac{c_m}{c_w} \quad (1)$$

In equation (1), $i_m$ is the peak current recorded with the membrane-coated sensor in an aqueous solution with a concentration of $c_w$; $i_w$ is the peak current measured in the same solution with an uncoated sensor; $D_m$ and $D_w$ are diffusion coefficients of the solute in the membrane and the aqueous solution; and $c_m$ is the concentration of the solute in the membrane. The calculation of $c_m$ and $P_{mw}$ (membrane/water partition coefficient) requires the knowledge of the diffusion coefficient of the solute in the membrane. By using diffusion coefficients measured in ion-selective membranes of similar composition ($D_m = 4 \times 10^{-8}$ cm$^2$/s) (Armstrong et al., *Electrochim. Acta* 35:1-7 (1990); Bodor et al., *Analyst* 133:635-642 (2008), each of which is hereby incorporated by reference in its entirety) and the experimentally measured $i_w/i_m$ ratio of ~140 (FIG. 13) in combination with $D_w = 8 \times 10^{-6}$ cm$^2$/s (Brookes et al., *J. Phys. Chem. B* 105:6361-6366 (2001), which is hereby incorporated by reference in its entirety) and $c_w = 1$ mM in Equation 1, $P_{mw} = 0.1$ was calculated for APAP, for PVC membrane I (o-NPOE). This is more than an order of magnitude smaller than the octanol/water partition coefficient values for APAP, ranging between $P_{ow} = 2.9$ and $P_{ow} = 1.6$. The partition coefficients calculated for membranes III (DOS) and V (1-octanol) using the same protocol were $P_{mw} = 0.5$ and $P_{mw} = 1.6$, respectively. Weber found a 1:1 correlation between the log $P_{mw}$ and log $P_{ow}$ values for membranes without background electrolyte and ion-exchanger (Chen & Weber, *Anal. Chem.* 79:1043-1049 (2007), which is hereby incorporated by reference in its entirety). Apparently the high concentration of background electrolyte and ion-exchange salt influence the extraction properties of the membrane.

Discussion of Examples 1-4

In the preceding Examples, several organic-film modified GC working electrodes are described for the quantitative assessment of physiologically relevant levels of propofol in serum-like electrolyte solutions. The membrane prevented fouling of the working electrode during propofol detection and improved the selectivity of the sensor due to the large difference in hydrophobicity between the analyte (propofol) and interfering compounds present in the sample, e.g., AA and APAP.

The sensitivity and selectivity of the membrane-coated working electrode for propofol is greatly influenced by the composition of the PVC membrane, i.e., the dielectric properties of the plasticizer, the selection and concentration of the background electrolyte, as well as the incorporation of mobile cation-exchange sites into the membrane, like TPFPhB$^-$. The membrane composition also affects the peak potential at which propofol is oxidized in the membrane.

The DL of CA measurements of propofol in PBS buffer (pH 7.2), and in PBS solutions containing 3 mM AA, 1 mM APAP and 5% BSA were 0.03 (±0.01) µM and 0.45 (±0.4) µM, respectively. These values are well below the physiologically relevant target concentrations used during anesthesia or sedation (Grossherr et al., *Brit. J. Anaesth.* 102: 608-613 (2009); Perl et al., *Brit. J. Anaesth.* 103:822-827 (2009), each of which is hereby incorporated by reference in its entirety).

Example 5—Real-Time Monitoring of Propofol

A series of additional experiments were performed using the preferred PVC membrane in a microfluidic detector cell.

Figure 14:
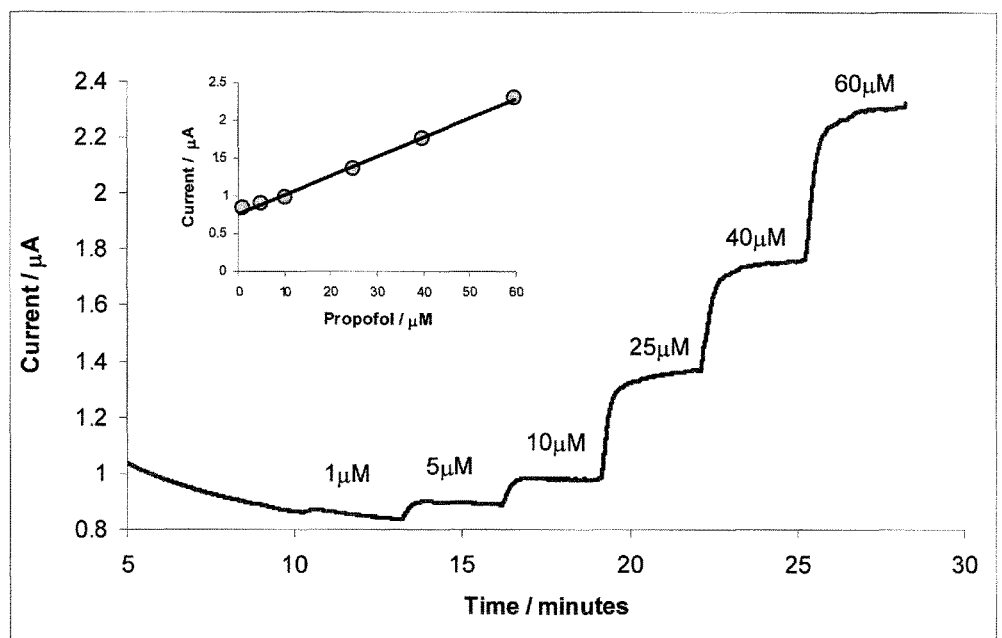
FIG. 14 shows the continuous CA monitoring of propofol. In this experiment propofol solutions with concentrations between 1 µM and 60 µM were pumped at constant flow rate through an electrochemical cell in which the working electrode was covered with the organic membrane film. Inset: A calibration curve constructed from the steady state currents measured at different concentrations of propofol.

FIG. 14 shows the results of a model experiment corresponding to continuous monitoring of propofol in PBS, which models the patient blood. PBS solution was pumped through a flow through detector cell, a Bioanalytical System Inc. flow cell modified to include the PVC membrane (spin-coated) over the electrodes to form an electrochemical cell. Output from the detector cell flowed back into the container. The measured current signal is proportional to the concentration to propofol in the sample in contact with the organic membrane coated electrode or electrochemical cell implemented in the flow through electrochemical cell. After approximately 10 minutes of recording the current signal in PBS without propofol, the propofol concentration in the sample container was increased ~every 3 minutes through the addition of propofol standard aliquots, while the sensor signal was continuously recorded. As the propofol concentration in the sample container increased the sensor signal also increased. From the steady state current signals recorded at different concentrations, a calibration curve was constructed (inset). Such a calibration curve can be used for the assessment of the propofol concentration in unknown samples.

Figure 15:
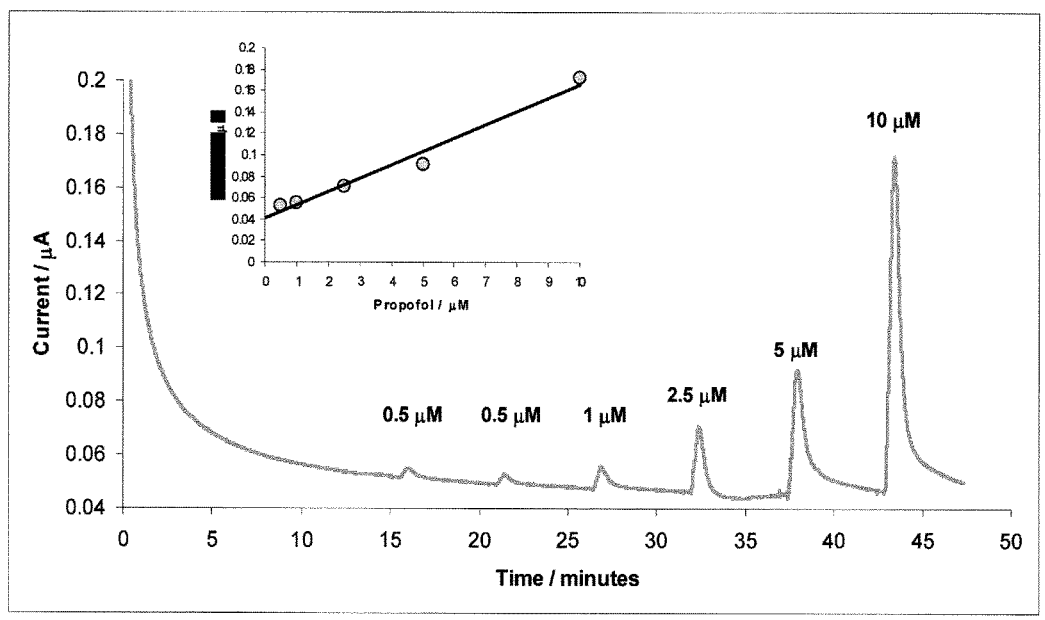
FIG. 15 illustrates the CA flow injection analysis of propofol solutions between 0.5 μM and 10 μM concentrations. In this experiment 100 μL samples of propofol solutions, with concentrations ranging between 0.5 μM and 10 μM, were injected into a continuously flowing carrier solution (PBS). As the injected sample plug passed the flow-through detector cell with the membrane coated propofol a transient signal is recorded. The peak height of these transients is directly proportional to the propofol concentrations in the injected samples. Inset: A calibration curve constructed from the peak heights as a function of the concentration of the injected samples.

FIG. 15 shows the results of a similar model experiment discussed in FIG. 14, i.e., a sample container filled with PBS models the patient blood. However, in this experimental model a carrier solution was pumped through the electrochemical flow cell and only small volume aliquots of the sample in the container are metered into the continuously flowing carrier solution. For metering small volume of samples into the carrier stream, sampling valves, also known as injectors, were used. The sample injected into the continuously flowing carrier stream traveled with the carrier through the flow-through electrochemical cell and generated a peak shape transient current signal. The peak height of the transient signal was proportional to the propofol concentration in the injected sample while the peak area was proportional to the total amount of propofol in the sample. This analysis method is known as flow-injection analysis (FIA) (see, e.g., Ruzicka & Hansen, *Flow Injection Analysis*, John Wiley & Sons, New York (1988), which is hereby incorporated by reference in its entirety). The peaks in the figure were recorded following the injection of samples with 0.5, 1, 2.5, 5 and 10 µM propofol concentrations. The inset shows a calibration curve constructed from the peak height—propofol concentration data pairs.

Figure 16:
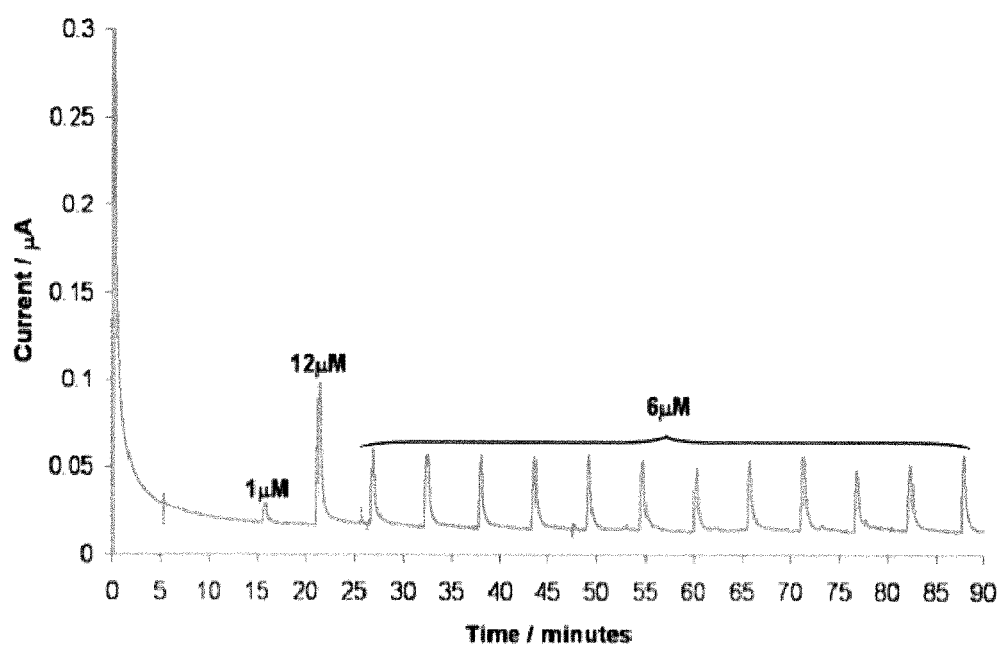
FIG. 16 illustrates the CA flow injection analysis of propofol solutions. Experimental conditions: Sample volume, 175 μL; Flow rate, 0.53 mL/min; applied potential, 1.2 V. 1 μM and 10 μM injections were used to construct a two-point calibration curve. Once the calibration was finished, the monitoring experiment started using 12× injections of 6 μM propofol in 5% BSA to simulate what is expected to be achievable using TCI. Injections into the carrier stream were performed at 5 minute intervals to determine the reproducibility of the propofol sensor when it is used in an automated analyzer in flow injection mode. The relative standard deviation was ~15%.

In a follow-up FIA experiment, sequential FIA was used to determine the concentration of propofol in samples. Peaks labeled in FIG. 16 as 1 µM and 10 µM correspond to the injection of 175 µL volume standard serum like solutions into a continuously flowing carrier steam as above. (Experimental conditions: Sample volume, 175 µL; Flow rate, 0.53 mL/min; applied potential, 1.2 V.) These injections were performed before the monitoring of propofol in model patient serum was started. The peak heights of these two transients were used to construct a two-point calibration curve. Once the calibration was finished, the monitoring experiment started. In the example of FIG. 16, for purposes of this model the patient serum propofol concentration remained constant at 6 µM concentration (which is expected to be achievable using, e.g., TCI). In the example, the 5% BSA containing sample was injected 12 times in the carrier stream with 5 minutes interval to determine the reproducibility of the propofol sensor when it is used in an automated analyzer in flow injection mode. The relative standard deviation was ~15%.

Figure 17:
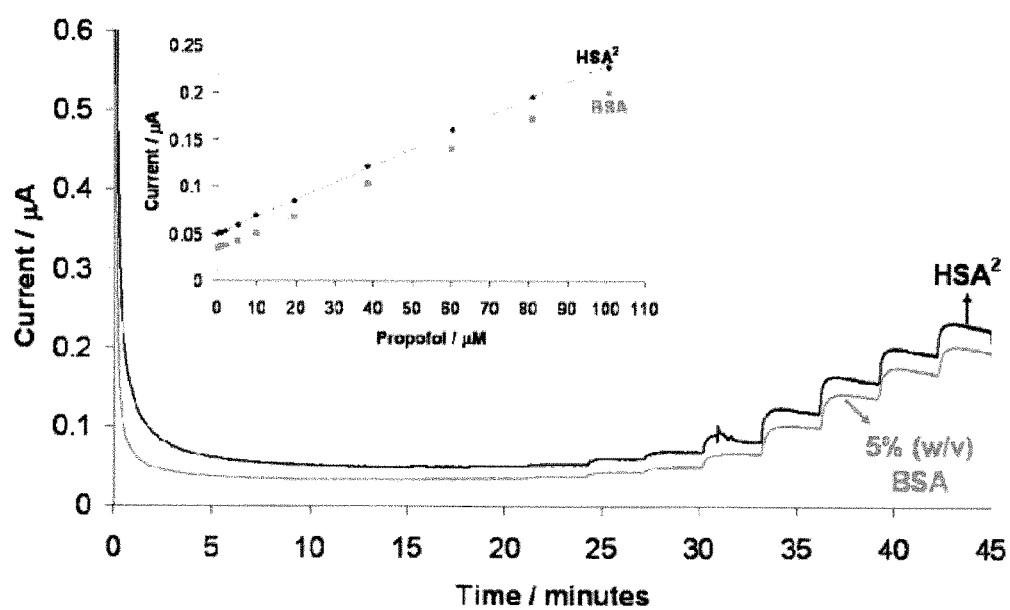
FIG. 17 illustrates continuous CA monitoring of propofol using human serum albumin (HSA) or 5% BSA containing electrolyte solution (simulating serum) with different concentrations of propofol pumped through the electrochemical flow cell.

In a final experiment, human serum (HSA) or 5% BSA containing electrolyte solution (simulating serum) with different concentrations of propofol were pumped through the electrochemical flow cell while the current signal of the organic membrane coated propofol sensor was continuously recorded. (Experimental conditions: Flow rate, 0.317 mL/min; applied potential, 1.2 V.) The inset to FIG. 17 shows the calibration curves constructed from the steady state current propofol concentration data pairs. FIG. 17 confirms that the 5% BSA containing standards can be used to assess the concentration in human serum samples.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An electrochemical sensor comprising:
   at least one electrode and a coating that surrounds the electrode, the coating comprising a structural component, a water immiscible solvent, a resistance decreasing component, and an ion exchange component,
   wherein the coating selectively partitions an electrochemically active drug from a fluid or vapor sample whereby an electrochemical signal within the coating can be measured using the electrode;
   wherein the coating comprises one or more of sodium tetrakis[3,5bis(trifluoromethyl) phenyl] borate (NaTF-PhB) and potassium tetrakis[pentafluorophenyl] borate (KTPFPhB) as the ion exchange component; and
   wherein the electrochemical sensor is a voltammetric sensor.

2. The electrochemical sensor according to claim 1, wherein the structural component comprises a polymer selected from the group of polyvinylchloride (PVC), silicone rubber, polyurethane, (meth)acrylate polymer, polypyrrole, polythiophene, polyoctylthiophene, polyanaline, polyvinyl pyrrolidone, agarose, hydrogel, sol-gel materials, or combinations thereof.

3. The electrochemical sensor according to claim 1, wherein the water immiscible solvent comprises 2-nitrophenyl octyl ether (o-NPOE), dioctyl sebacate (DOS), bis(2-ethylhexyl) sebacate, benzyl 2-nitrophenyl ether, bis(1-butylpentyl) adipate, bis(2-ethylhexyl) adipate, bis(2-ethylhexyl) phthalate, 1-chloronaphthalene, chloroparaffin, 1-octanol, 1-decanol, dibutyl phthalate, dibutyl sebacate, dibutyl-dilaurate, dodecyl 2-nitrophenyl ether, or combinations thereof.

4. The electrochemical sensor according to claim 1, wherein the resistance decreasing component is an organic salt that is not soluble in water and comprises a lipophilic cation and a lipophilic anion.

5. The electrochemical sensor according to claim 4, wherein the lipophilic cation is selected from the group consisting of tetradodecylammonium, tetraphenylphosphonium, bis(triphenylphosphoranylidine) ammonium, dimethyldioctadecyl ammonium, hexadecyltrioctadecylammonium, methyltrioctadecylammonium, tetrahexadecylammonium, tetraoctadecylammonium, tetraoctylammonium, tridodecylmethylammonium, tris[(perfluorooctyl)propyl]ammonium, and combinations thereof.

6. The electrochemical sensor according to claim 4, wherein the lipophilic anion is selected from the group consisting of tetraphenylborate, tetrakis(pentafluorophenyl) borate, tetrakis(4-chlorophenyl) borate, tetrakis [3,5,bis(trifluoromethyl) phenyl] borate, tetrakis(4-fluorophenyl) borate, dinonylnaphthalene sulphonate, tetrakis [3,5-bis(perfluorohexyl)phenyl]borate, tetrakis(p-tolyl)borate, tetrakis (m-tolyl)borate, tetrakis(2,4-dimethyl)borate, tetrakis(3,5-dimethylphenyl)borate, closo-dodecacarborane, undecachlorinated carborane (UCC), hexabrominated carborane (HBC), undecaiodinated carborane (UIC), undecabromocarborane, and combinations thereof.

7. The electrochemical sensor according to claim 4, wherein the organic salt is tetradodecylammonium tetrakis (pentafluorophenyl) borate (TDDATPFPhB), bis(triphenylphosphoranylidene)ammonium tetrakis [3,5,bis (trifluoromethyl)phenyl]borate (BTPPATFPhB), tetradodecylammonium tetrakis(4-chlorophenyl)borate, tris [(perfluorooctyl)propyl]ammonium tetrakis [3,5-bis(perfluorohexyl)phenyl]borate, tetraheptylammonium tetraphenylborate, tetradodecylammonium dinonylnaphthalene sulphonate, tetraphenylphosphonium tetraphenylborate, tetraphenylphosphonium tetrakis(penta-fluorophenyl)borate, tetraphenylphosphonium tetra-p-tolylborate, tetraphenylphosphonium tetra-m-tolylborate, bis(triphenylphosphoranylidene)ammonium tetraphenylborate, bis(triphenyl-phosphoranylidene)ammonium tetrakis(penta-fluorophenyl) borate, bis(triphenyl-phosphoranylidene)ammonium tetrakis(4-chlorophenyl)borate, bis(triphenylphosphoranylidene) ammonium tetrakis[3,5,bis(trifluoromethyl)phenyl]borate, bis(triphenylphosphoranylidene) ammonium tetrakis(4-fluorophenyl)borate, hexadecyltri octadecylammonium tetraphenylborate, tetraoctadecylammonium tetraphenylborate, tetraoctadecylammonium tetrakis(4-chlorophenyl)borate, tetraoctadecylammonium tetraphenylborate, tetraoctadecylammonium tetrakis(4-chlorophenyl)borate, tetraoctadecylammonium tetrakis(4-fluorophenyl)borate, tetraoctylammonium tetraphenylborate, tetraoctylammonium tetrakis(pentafluorophenyl)borate, tetraoctylammonium tetrakis (4-chlorophenyl)borate, tetraoctylammonium tetrakis [3,5, bis(trifluoromethyl)phenyl]borate, tetraoctylammonium tetrakis (4-fluorophenyl)borate, tridodecylmethylammonium tetraphenylborate, tridodecylmethylammonium tetrakis(pentafluorophenyl)borate, tridodecylmethylammonium tetrakis (4-chlorophenyl)borate, tridodecylmethylammonium tetrakis [3,5,bis(trifluoromethyl)phenyl]borate, tridodecylmethylammonium tetrakis(4-fluorophenyl)borate, tridodecylmethylammonium dinonylnaphthalene sulphonate, dodecyltrimethyl ammonium dinonylnaphthalene sulphonate, tetrabutylammonium tetraphenylborate, tetrabutylammonium tetrakis(pentafluorophenyl)borate, tetrabutylammonium tetrakis(4-chlorophenyl)borate, tetrabutylammonium tetrakis(4-fluorophenyl)borate, tetrabutylammonium tetrakis [3,5,bis(trifluoromethyl)phenyl]borate, tetraphenylphosphonium tetraphenylborate, trimethylammonium undecabromocarborane (TMAUBC), and combinations thereof and combinations thereof.

8. The electrochemical sensor according to claim 1 comprising PVC as the structural component; at least one of 2-nitrophenyl octyl ether (o-NPOE), dioctyl sebacate (DOS), and 1-octanol as the water immiscible solvent; and tetradodecylammonium tetrakis(pentafluorophenyl) borate (TDDATPFPhB) or bis(triphenylphosphoranilidine) ammonium tetrakis [3,5,bis (trifluoromethyl) phenyl] borate (BTPPATFPhB) as the resistance decreasing component.

9. The electrochemical sensor according to claim 8 wherein: PVC is present in an amount of about 20 to 30 wt. percent, o-NPOE, DOS, or 1-octanol is present in an amount of about 45 to 55 wt. percent, TDDATPFPhB or BTPPATFPhB is present in an amount of about 20 to 25 wt. percent, and NaTFPhB or KTPFPhB is present in an amount of about 2 to about 4 wt. percent.

10. The electrochemical sensor according to claim 1 further comprising a biocompatibility enhancing component selected from the group consisting of nitric-oxide releasing sol-gel materials, N-(6-aminohexyl)aminopropyltrimethoxysilane, and balanced isobutyltrimethoxysilane diazeniumdiolate.

11. The electrochemical sensor according to claim 1, wherein the lower limit of detection of the bioavailable drug in blood or serum is less than the target steady state concentration of the drug in blood or serum.

12. The electrochemical sensor according to claim 1, wherein the drug is propofol and the sensor can detect propofol concentrations at 0.03 µM or greater.

13. The electrochemical sensor according to claim 1, wherein the drug is propofol and the limit of detection in blood or serum is about 1 to about 2 orders of magnitude below a therapeutic range for propofol.

* * * * *